United States Patent [19]

Moore et al.

[11] Patent Number: 4,987,539
[45] Date of Patent: Jan. 22, 1991

[54] APPARATUS AND METHOD FOR MULTIDIMENSIONAL CHARACTERIZATION OF OBJECTS IN REAL TIME

[75] Inventors: Wayne A. Moore, San Francisco; Tom Nozaki, Jr., Palo Alto; David R. Parks, San Francisco; Richard T. Stovel; Gary Breitbard, both of Palo Alto, all of Calif.

[73] Assignee: Stanford University, Stanford, Calif.

[21] Appl. No.: 82,254

[22] Filed: Aug. 5, 1987

[51] Int. Cl.[5] ............................................. G06F 15/42
[52] U.S. Cl. .............................. 364/413.08; 356/39; 356/72; 209/579; 364/555
[58] Field of Search .................. 364/555, 413.08, 478; 209/3.1, 3.3, 579; 436/63, 172, 164; 422/73; 356/318, 72, 39; 382/6, 37

[56] References Cited

U.S. PATENT DOCUMENTS

| | | | |
|---|---|---|---|
| 3,710,933 | 1/1973 | Fulwyler et al. | 209/579 |
| 3,826,364 | 7/1974 | Bonner et al. | 209/579 |
| 3,851,156 | 11/1974 | Green . | |
| 3,864,571 | 2/1975 | Stillman et al. | 250/302 |
| 3,941,479 | 3/1976 | Whitehead | 356/335 |
| 3,976,862 | 8/1976 | Curbelo | 364/555 |
| 4,184,766 | 1/1980 | Hugg | 364/555 X |
| 4,193,115 | 3/1980 | Albus | 364/513 X |
| 4,318,184 | 3/1982 | Millet et al. | 364/900 |
| 4,514,816 | 4/1985 | Ollus et al. | 364/478 |
| 4,566,595 | 1/1986 | Fustier | 209/545 |
| 4,573,796 | 3/1986 | Martin et al. | 356/318 |
| 4,596,464 | 6/1986 | Hoffman et al. | 356/336 |
| 4,610,361 | 9/1986 | Elliot | 209/555 |
| 4,649,494 | 3/1987 | Rosas | 364/478 |
| 4,661,913 | 4/1987 | Wu et al. | 364/500 |
| 4,667,830 | 5/1987 | Nozaki, Jr. et al. | 209/3.1 |
| 4,700,294 | 10/1987 | Haynes | 364/200 |
| 4,778,593 | 10/1988 | Yamashita et al. | 209/3.1 |
| 4,833,629 | 5/1989 | Moore | 364/555 |

OTHER PUBLICATIONS

"High Speed FIFO's Contend with Widely Differing Data Rates", Miller et al., Computer Design 9/1/85, pp. 83–86.
Discrete Mathematics, pp. 418–421, 426–428 (trees), Ross & Wright, Prentice-Hall.
Parks et al. (1984), Methods of Enzymology 108, pp. 197–241.
Parks et al., in Handbook of Experimental Immunology, 4th edition, (D. R. Parks et al., ed.), Blackwell Scientific Publication, Oxford, England, 1986, pp. 29.1–29.21.
Parks et al. (1984), Cytometry 5:159–168.

Primary Examiner—Parshotam S. Lall
Assistant Examiner—S. A. Melnick
Attorney, Agent, or Firm—Ronald C. Fish

[57] ABSTRACT

A system for characterizing objects to be sorted in real time and making sorting decisions using lasers to excite fluorescing dyes used to tag objects such as cells which flow through the laser beam in a stream of conductive fluid. The scattered light and fluorescent light at various frequencies define a multidimensional space. These light characteristics are sensed and digitized. The data so gathered is buffered and then compared to a binary classification tree. The individual parameters cause a certain path through the binary decision tree to be taken while the cell is passing from the point in the stream where the light characteristics are gathered to a point where electrostatically charged electrodes deflect individual statically charged drops containing cells to be sorted into various sorting bins. When the decision tree has been traversed, the sorting decision for the drop containing the cell which had those parameters is done. This sorting decision is buffered until the time the drop reaches the charged electrodes. The sort decision is then accessed and used to properly charge the electrodes so that the drop is diverted into the proper bin.

35 Claims, 7 Drawing Sheets

APPARATUS AND METHOD FOR MULTIDIMENSIONAL CHARACTERIZATION OF OBJECTS IN REAL TIME

BACKGROUND OF THE INVENTION

The invention relates to the field of real time sorting systems for rapid collection of data about objects or signals, arrangement of that data into a multidimensional space vector, characterization of the object based upon its signature from the multidimensional space vector and directing an output device to carry out a sort decision or other action to characterize the object or signal. A specific application of the system is in the field of cell sorting for biological research where a stream of dyed cells is passed through a laser beam, scatter and fluorescence data is collected and each cell's phenotype is established in real time by a computer comparison of the data After the phenotype is established, a sort decision is made and carried out.

There are many fields where real time sorting or characterization of rapidly occurring events is necessary. Those skilled in the art of real time sorting of objects based upon characterizing the objects using a multidimensional binary sort tree will appreciate the types of applications which are in need of a system such as the one disclosed herein.

In the field of biological research, it is useful to be able to sort large numbers of different cells into different phenotypes characterized by different properties. This process cannot be done by hand. Automated cell sorters were developed in the last 20 years to sort several thousand cells per second passing an inspection point in a stream of liquid. These machines used electrostatic droplet deflection technology originally developed for ink jet printers. Early versions of such sorters used laser beams shining on a stream of liquid carrying the cells of interest. The cells had been dyed with dyes which exhibited fluorescence. These cells would both absorb and scatter the laser light as they passed the beam. The dyes on the cells would be excited by the laser light and fluoresce, i.e., emit light in certain bands of wavelengths as the cells moved further in the stream.

This scattered and fluorescent light was collected by sensors and analyzed by analog circuitry. Because certain dyes were bound chemically to certain antibodies and because those antibodies would only bind to certain proteins on the surface of the cells of interest, each cell would have a unique phenotype expressed in terms of the light scattering and emission properties of the cell with its fluorescent tag. Such phenotypes could be used to make sorting decisions to enable sorting of the cells into physically separate collection containers. This was done in the prior art by generating a sort decision and using it to charge a drop containing the cell. Each drop would be charged with a charge having a polarity such that the drop could be deflected into the proper collection container when the drop passed through an electrical field between two electrically charged high voltage plates. These plates had a potential difference between them which created an electric field of a polarity to deflect the trajectory of the drop containing the cell having a particular phenotype into the corresponding collection container. Charging and formation of the drops was done by vibrating a nozzle the cells passed through. An electrode was placed in the stream of liquid. This electrode was coupled to the sorting circuitry and could be charged to any of a number of different states. The vibration of the nozzle caused the emerging liquid jet to be broken into thousands of individual, uniform droplets. These droplets were charged with whatever charge was on the electrode at the time the droplet broke from the jet.

The structure and operation of these early analog sorters is more fully described in U.S. Pat. No. 3,826,364 and in Chapter 19 of Volume 108 of the *Methods in Enzymology* series, by D. R. Parks and L. A. Herzenberg entitled, *Fluorescence-Activated Cell Sorting: Theory, Experimental Optimization, and Applications in Lymphoid Cell Biology*, Academic Press, Orlando, Fla. (1984). Another reference useful for understanding the background of and foundation technology for cell sorting, also called flow cytometry, is Chapter 29 of the *Handbook of Experimental Immunology*, 4th edition by D. R. Parks, L. L. Lanier & L. A. Herzenberg entitled *Flow Cytometry and Fluorescence Activated Cell Sorting (FACS)*, Blackwell Scientific Publications, Oxford, England (1986). Machines to do such sorting are commercially available from Becton Dickinson as the FACS I, FACS II, FACS III, FACS IV, FACS 400, FACS 420, FACS 440 and FACSTAR. Some of these machines have been in use at Stanford University in the Department of Genetics for many years, and the details of their design are well known. Other companies also make flow cytometry machines available to the public. These publications and the knowledge embodied in these machines are hereby incorporated by reference.

The trend in flow cytometry is toward multiparameter measurements using multiple laser wavelengths exciting multiple dyes with differing emission spectra so as to enable more sophisticated and powerful analysis. In the prior art, people have generally been collecting only two or three dimensional data consisting of forward scatter and one or two wavelengths of fluorescence. This data was either analyzed using analog circuitry or digitized and used as indices in a look up table which stored sort decisions for various phenotypes characterized by various scatter and fluorescence parameters. The sorting decisions were then output into a buffer to await arrival of the droplet containing the cell to which each sort decision applied at the sorting apparatus of the machine. Output of sorting decisions from the buffer to the electronic circuitry that controlled the charging of the droplets was based upon a digitized index value for each cell. This index value was based upon the time of arrival of the cell in the area of the machine where it was excited by the laser beam.

The problem with this approach was that the sophistication of the phenotype sorting decision was limited, and the sorting decision was somewhat inflexible in the analog case since new sorting decision processes had to be implemented in new analog hardware.

These limitations led people to search for more sophisticated and flexible systems. One step was to increase the number of lasers and dyes used so that additional properties could be measured for each cell, resulting in additional dimensions in the data vector for each cell. These developments are described in a paper by D. R. Parks, R. R. Hardy and L. A. Herzenberg from the Stanford University Department of Genetics in the School of Medicine, entitled "Three-Color Immunofluorescence Analysis of Mouse B-Lymphocyte Subpopulations" published in *Cytometry*, Vol. 5, p. 159 (1984). With such data, much more sophistication of analysis was possible and more phenotypes could be distinguished. This paper is hereby incorporated by reference.

The ability to collect multiple parameters in multidimensional space, i.e., space having more than two dimensions has led to severe complications in trying to use prior art analog and digital systems to make sort decisions on this type of data in real time and with sufficient flexibility to be able to easily change the methodology of the sorting decision. Analog systems must be extremely complex to implement this type of sort decision and can implement only one type of analysis for a given design of the analog sort decision hardware. If a different type of analysis is desired, new sort decision hardware has to be built.

Prior art digital flow cytometry systems using lookup tables cannot handle multidimensional space data having three or more dimensions. Array look up algorithms do not extend well to multidimensional space. Such array look up flow cytometry systems require prohibitive amounts of memory which memory demand increases exponentially when more dimensions are to be considered in sort decisions.

Further, all prior art devices known to the inventors require a cell to pass in front of both lasers before the peak detect and sampling circuitry can be released to deal with another cell. This need for each cell to pass in front of both lasers before it could be classified caused a blind spot in prior art devices during which no other events could be detected and no other cell could be classified. This blind spot had a duration equal to the travel time for the cell to pass in front of both lasers.

Further, there is no prior art sorter which can receive compensation signals from more than one channel, sum the compensation signals and use the composite signal for compensation purposes.

Thus a need has arisen for a cell sorting system which can be fast enough to operate in real time on multidimensional space vectors and flexible enough to allow differing analysis and decision making processes to be implemented easily without difficult, time consuming and expensive modification of the apparatus.

As far as applicants know, there is no prior art system wherein sorting decisions can be made without the need for a cell to pass in front of both lasers. Also, there is no prior art cell sorter system wherein the compensation circuitry for each channel can receive compensation signals from more than one other channel to eliminate cross talk resulting from dye emissions from more than one other channel falling within the passband of the channel being compensated.

SUMMARY OF THE INVENTION

The invention is a buffered, asynchronously operating digital classification system which can operate on multidimensional data arranged as vectors in multidimensional space using multidimensional binary search trees. The tree is generated by a "host processor" which aids the user to manually process test data from a small sample run of cells from the group of cells to be classified by the system of the invention. The test data is in the form of multidimensional vectors. This data is presented to the user for analysis so that manual classification decisions may be made based upon characteristics of various subpopulations in the test group of cells. After the user manually defines how the sort decisions are to be made for the phenotypes in the test group based on the test data, the host processor uses the manual decisions and generates a binary classification tree for use by the system of the invention for automatically making sort decisions and sorting the balance of the cells in the sample.

The binary classification tree is then transferred to a "sort processor" which controls the sorting apparatus. The sort processor takes the raw data coming in from the detectors in the laser illumination area as the cells in the population of cells to be sorted pass through the laser beams and uses the data to make sorting or classification decisions in real time. The host processor allows the user to make the manual sort decisions on the test data based upon any analysis procedure desired. Any manner in which the binary classification tree is generated will suffice for purposes of practicing the invention.

The advantage of this system is that completely different classification approaches based upon pattern recognition and/or decision theory can be easily implemented in the binary classification tree, and the system of the invention can then do the sorting based upon the binary classification tree without any change in the hardware of the sorting system.

After the binary classification tree is loaded into the sort processor, the incoming vectors describing the cells being sorted have their elements compared against the decision nodes in the classification tree until the vector has been completely processed and a sorting decision is made. The decision is then output to a FIFO buffer for temporary storage. At the time the cell corresponding to a particular sort decision reaches the sorting area of the machine, the sort decision is read out of the FIFO buffer and acted upon.

According to the teachings of the invention, the sort processor and its associated data gathering and sorting apparatus represent one way of using binary classification trees to make real time sorting decisions on streams of events of high volume. Applications of this technology are not limited to flow cytometry. Hereafter, the sort processor and its associated data gathering and sorting apparatus will sometimes be referred to as the real time classification processor.

On the input side of the real time classification processor is a general data collection apparatus which senses certain parameters which characterize a particular event, such as the phenotype of the cell, and digitizes the data. The event may be a signal, a data word or object such as a human cell. The digitized data values for each parameter are then stored in a separate FIFO buffer for each different type of parameter. There is a separate FIFO for each element of the multidimensional vector, and each FIFO represents one data channel. In the preferred embodiment, there are 8 data channels.

When an event occurs such as a cell passing through the laser beams, the data for each parameter of the object or event is read by the detector apparatus of the real time classification processor and the resulting vector is buffered in the aforementioned FIFO's. When the real time classification processor is ready to characterize a particular event or object, the vector data is taken out of the FIFO's and comparisons are made to the classification conditions implemented in the nodes of the binary classification tree. The real time processor continues to compare the various parameters in the input vector to the nodes in the tree until it arrives at a sort decision regarding the particular cell which generated the data.

The advantage of this system is that the time it takes to make a sorting decision increases linearly instead of exponentially with increased dimensions or parameters which are being measured to characterize the various phenotypes to be sorted. Further, the system of the invention can make complex classification decisions on eight dimensional data in less time than it takes to do the same thing using prior art technology.

DETAILED DESCRIPTION OF THE PREFERRED EMBODIMENT

Figure 1:
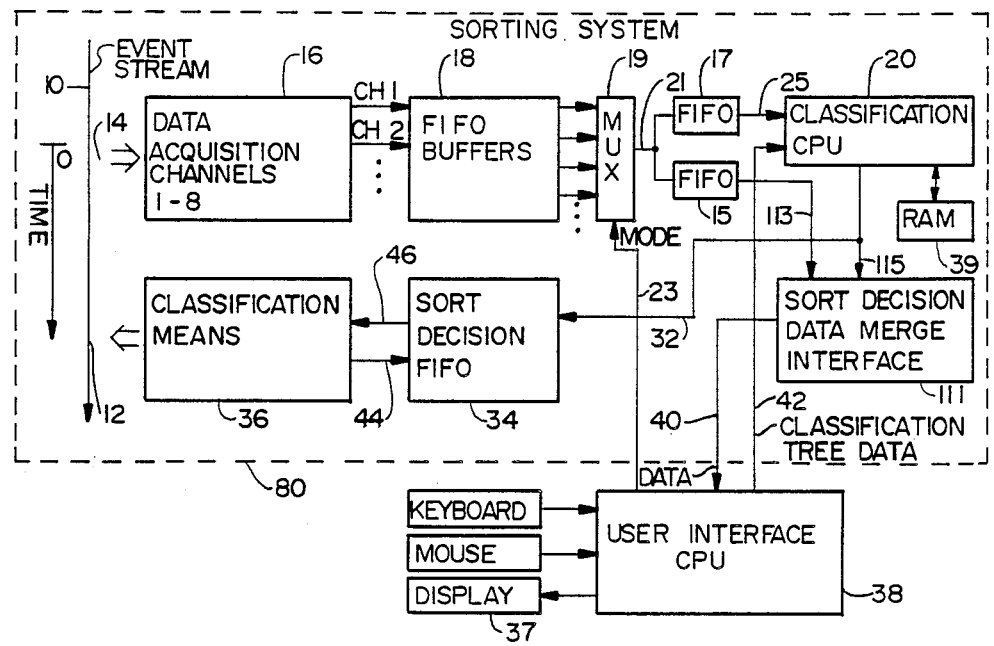
FIG. 1 is a block diagram of a general system designed according to the teachings of the invention.
Figure 2:
FIG. 2 is a symbolic diagram of a multidimensional space vector comprised of a plurality of components each of which represents data which can be generalized as the coordinate for a particular object or event on that axis of multidimensional space.

Referring to FIG. 1 there is shown a block diagram of the generic invention which is useful for making real time classification decisions regarding a stream of events in any one of a number of different fields where the frequency of occurrence of the events and varying analysis needs dictate the use of digital computers.

Typically, the invention will work in an environment involving a stream 10 of events which need to be sorted or otherwise classified based upon data gathered about the event. These events could be of many different types depending upon the field of use, and will require a classification action performed at a point 12 in the stream. The sort decision must be made during the time it takes the droplets to travel from a point 14 where data characterizing the event is gathered to the point 12 where the sorting action must be taken. Typically, this travel time is 100 to 200 microseconds.

The types of events for which the system may be used in various embodiments is varied. For example, the events could be the passage of cells dyed with certain fluorescent dyes before one or two laser beams. Another example would be the arrival of images or preprocessed data from a video stream processing system. Whatever the event, a data acquisition means 16 analyzes the event stream at a point in time 14 and generates a multidimensional vector in multidimensional space consisting of 2 or more components of digital data. Because of the wide variety of fields of use of the invention, it is not possible to specify all the possible structures for the data acquisition means 16. However, those skilled in the art of practicing data acquisition in any of the particular fields of use to which such a real time classification system would find use will appreciate the apparatus needed to analyze their particular event stream. One particular embodiment of the data acquisition means in the flow cytometry field is described herein and other embodiments are described in the papers and other references incorporated herein by reference. In the field of computer vision inspection systems, the data acquisition means 16 might include a plurality of pattern recognition circuits, each designed to look for a specific defect such as excess or missing metal, pinholes and misalignment of mask registration marks in a series of rapidly arriving video images of a die for a particular type of integrated circuit. Whatever the field of use, the data acquisition means 16 should sense two or more parameters characterizing each event and digitize the values.

The digital values characterizing each parameter are stored in a FIFO buffers 18, and are passed to the FIFOs from the data acquisition channels 1-8 via the buses marked channels 1-8. Preferably, there is a separate FIFO buffer for each parameter to enable parameters detected slightly downstream from earlier detected parameters to be assembled into a single multidimensional space vector despite slight differences in times at which the individual components are digitized and stored in their individual buffers. Since the buffers are FIFO, their relative positions in the buffers indicate which event in the stream they characterize despite different storage times for each parameter. Each parameter from an event is stored with a count indicating the event number to facilitate correlation of the data being read out of the FIFOs 18 to keep all the parameter data from one event together as one data packet. The event count data is supplied by a counter in the data acquisition channels 16 which is normally coupled to detect and count the event pulse resulting from forward scattered light in flow cytometry applications. The structures for such FIFO buffers are well known in the art.

The use of a separate FIFO 18 for each parameter of each event allows the classification processor 20 to make classification decisions on events which are spaced closely together in time without losing data. The reason for this will become clear below in connection with the discussion of the separate delay shift registers in each data acquisition channel in FIG. 7 to set the timing between event detection and signal peak sampling.

The event data in the form of the parameter data stored in the FIFOs 18 are read out of the FIFOs by a multiplexer 19. The multiplexer 19 has one input coupled to the output of each FIFO in the FIFO buffers 18 and an output coupled to the inputs of dual FIFOs 15 and 17. The multiplexer 19 is a self directed scanning multiplexer in that it controls its own selection of which input to couple to its output 21. The multiplexer 19 has a mode register which is coupled to a mode bus 23 from the user interface CPU 38. The mode bus 23 carries data regarding which of the parameters is to be taken from the FIFO buffers 18 and loaded into the FIFOs 17 and 15. Not all classification processes require use of all the parameters that the system can gather. The particular parameters involved in a particular classification process will hereafter be collectively referred to as the mode. The mode data on the bus 23 is latched into the mode register (now shown) inside the multiplexer 19 and is used by scanning circuitry (not shown) inside the multiplexer 19 to control the select inputs of the multiplexer 19. That is, if only parameters 1, 2 and 5 are to be used in the classifications decisions of a particular population of events, the mode register in the multiplexer 19 is loaded with data indicating only parameters 1, 2 and 5 for each event are to be taken out of the FIFO buffers 18 for the data acquisition channels. The multiplexer 19 then controls its own selection of inputs to sequentially couple first the input from channel 1, then the input from channel 2 and then the input from channel 5 to the output 21. All the other inputs are ignored.

The FIFO 17 is coupled to a classification processor 20 via a bus 25. The FIFO 17 provides buffering for the classification processor 20. Then when the classification processor has a difficult classification decision to make, it may take as long as necessary to make the decision without losing data from other events which occur while the classification processor is working on classifying a previous event.

The FIFO 15 serves the same purpose for the user interface CPU 38. The raw data collected from the stream of events is, in the preferred embodiment, sent to the user interface CPU 38 via bus 113, sort decision data merge interface 111 and bus 40 for graphic display on a display 37. This is not necessary to the classification process, and may be eliminated in some embodiments. In the preferred embodiment, the user interface CPU 38 takes the raw data from the FIFO 15 in pairs and plots the event data pairs in separate windows on the display 37 using the values of the parameters in each pair for an event as x and y coordinates for the displayed manifestation of that event.

The classification processor 20 compares the parameter data for each event to the nodes of a binary classification tree to make the classification decision. The binary classification tree data is stored in random access memory 39, and is supplied to the classification processor 20 via the bus 42 from the user interface CPU 38. In some embodiments, the binary classification tree data is manually generated based upon the typical parameters found in a sample population of the events to be classified which have been manually examined by a researcher. After the researcher decides how he or she wishes to classify other events in the population of events to be classified and sorted, these decisions are encoded manually in some embodiments into a binary classification tree. The data describing this tree is then supplied on the bus 42 as a serial stream of words which together define a data base.

Figure 3:
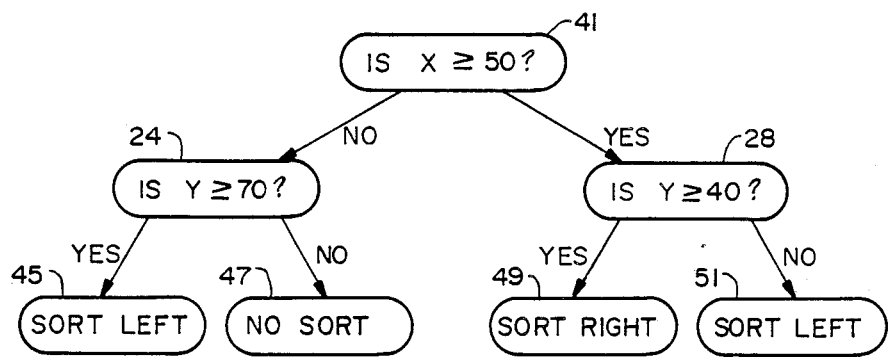
FIG. 3 is an example of a binary classification tree in two dimensional space having only x and y axes.
Figure 4:
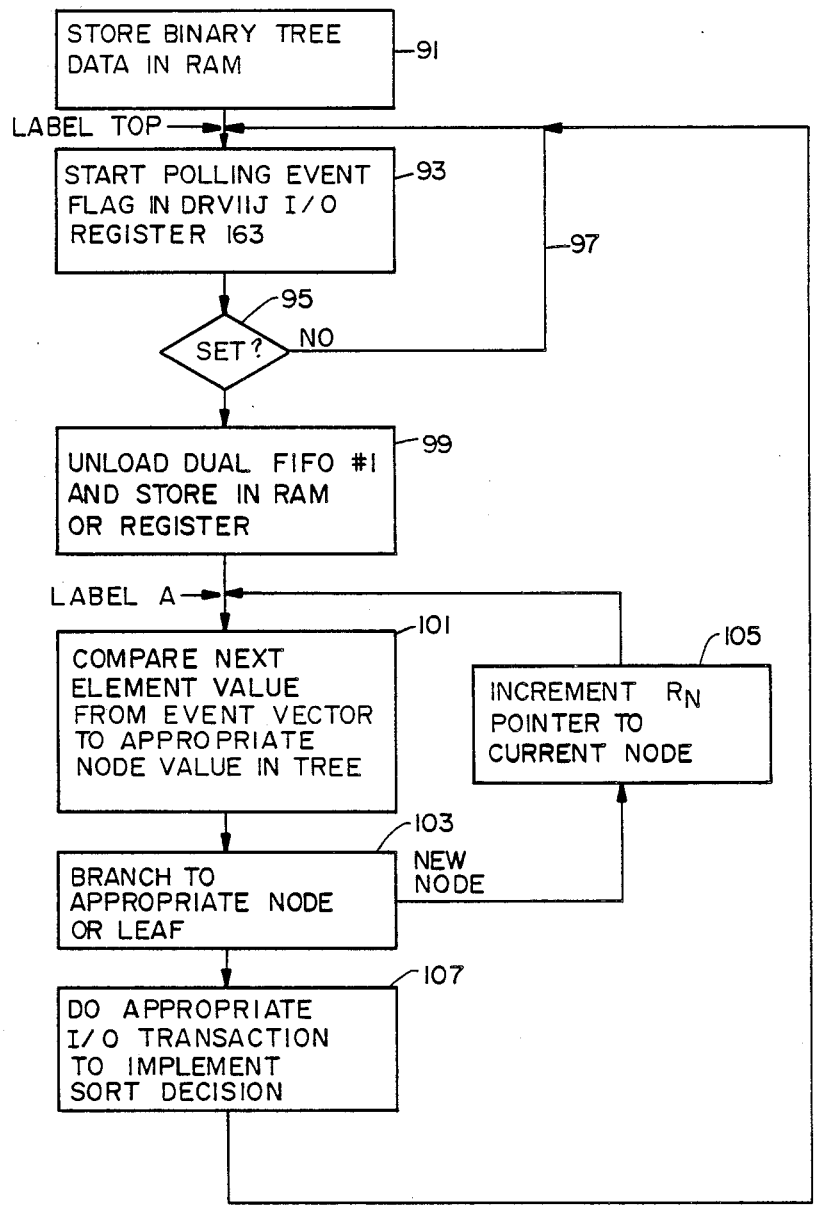
FIG. 4 is a flow chart of the process performed in real time by the classification processor in classifying events and performing an I/O operation to the sorting apparatus.

A classification tree structure for vectors in two dimensional space is symbolized in FIG. 3, and the resulting classification in two dimensional space is illustrated in FIG. 4. Each binary classification tree takes the form of a data base with one data record for each node of the tree and one data record for each leaf or terminating node in tree. Each data record is comprised of 4 fields. The first field stores data indicating to which parameter the node pertains. The second field stores the constant against which the value for that parameter for a particular event is compared to traverse the branches of the tree. The last two records in each record are pointers to the next record in the data base to process when the results of the comparison indicate the parameter value is less than or more than the constant value. One of the conditional branches will also occur when the parameter value is equal to the constant, and which one will occur is defined by the user.

Figure 6:
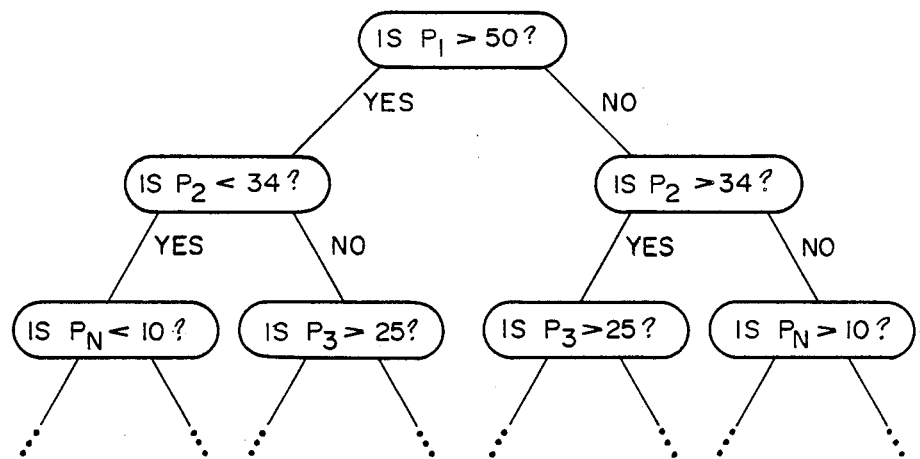
FIG. 6 is an example of a classification tree in multidimensional space.

In FIG. 3, the nodes of the binary tree are shown at 41, 24 and 28, and the leaves of the tree are shown at 45, 47, 49 and 51. An extension of the binary classification tree concept to n parameters, i.e., n dimensional space, is shown at FIG. 6. Note however, that although the trees of FIG. 3 and 6 all show the same parameter being compared to constants on any given level of the tree, this need not necessarily always be the case. That is, in the tree of FIG. 6, although the second level of the tree only $P_2$ parameters are being compared, in other trees it may be true that the left branch from the first level of the tree may be a $P_2$ comparison while the right branch from the first level is a $P_3$ comparison.

Generally, the leaf nodes in a binary classification tree are the sort decision nodes which indicate which way an event is to be sorted because of the results of the comparisons made between the actual parameter data collected about an event and the constant values assigned to the nodes of the binary classification tree.

Each node and leaf in the binary classification tree is represented in RAM 39 as a record in a data base. Each record has two linking fields and a field which stores the constant value for the node, if the record is for a node, or the sort decision, if the record is for a leaf.

The process the real time classification processor 20 performs in comparing the parameter data to the nodes of the binary classification tree is illustrated in FIG. 4 which is a flow chart of the steps of a real time classification and sort process. The first step is shown at 91 which symbolizes the process of receiving the binary tree data records on the bus 42 and storing these records as a data base in RAM 39. Preferably, the binary tree records are stored by DMA transactions.

The next step is symbolized by block 93 indicating that polling of the event flag in the DRV11J I/O register begins. The classification system is not interrupt driven, but is a polled implementation. The event flag is a bit in a status register (FIG. 7; not shown on FIG. 1) which is set by a control signal from FIFO 17 in bus 25 indicating that data is present in FIFO 17 to be processed by the classification processor 20. The FIFO 17 is of a design such that whenever it is loaded with the data from at least one parameter describing an event, a control signal is activated which sets the event flag bit in the status register of the classification processor 20. The status of the event flag bit is tested at step 95 and a branch back to step 93 is made if the flag is not set via path 97. If the flag is set, a branch to a step 99 is made where the parameters characterizing the next event to be processed are unloaded from the FIFO and stored in an internal register of the processor or in the external RAM 39.

Comparison of the first parameter used in the binary tree at level 1 is then performed as symbolized by step 101. In the tree of FIG. 3, level 1 is the level of the node 41 and level 2 is the level of nodes 24 and 28 and so on. Thus, step 101 for the tree of FIG. 3 represents the steps of doing an I/O instruction sequence to get the data record for the level 1 node and then accessing the particular parameter identified by the appropriate field of the first level node data record. Then the classification processor 20 compares the x value of the parameter to whatever constant is stored in the appropriate field of the level 1 node data record. In this case, that constant value is 50. Processing then proceeds to step 103.

Step 103 represents the process of using the results of the comparison to branch either to a new node to traverse the tree or to a leaf to implement a sort decision. If the branch is to a new node, step 105 is performed to increment a pointer designated $R_n$ to point to the current node in the tree being processed. Processing then branches back to label A and step 101 is performed again to access the data record for the next node and to compare the appropriate parameter data to the constant stored in the constant field of the node data record for the current node. The branch to the new node is accomplished by reading the appropriate pointer field in the data record for the current node based upon the results in the comparison and setting $R_n$ to the address of the new node to be processed using the contents of the pointer field.

If the branch from step 103 is to a leaf, step 107 is performed to do the appropriate I/O instruction to output a value to the sort decision FIFO 34 via bus 32. This value is converted by the classification means 36 to an appropriate action to implement the sorting decision. In the case of flow cytometry, the sort decision is implemented by appropriately charging the drop deflection plates to deflect the trajectory of the drop containing the cell which generated the parameter data upon which the sort decision is based into the proper container. Processing then branches to step 93 to begin the polling process again for the next event.

At the beginning of a sort run, the user interface CPU 38 queries the user regarding which parameters about an event are to be used in the classification decision. The processor 38 is a programmed DEC MICROVAX in the preferred embodiment. It should be understood that the invention is not limited to the particular computer and programming used for the user interface CPU 38 since the control signals to control the system and send the classification tree data can be supplied to the sorting system of the invention from other sources as well.

It should be further understood that any apparatus or a human may generate the binary classification tree database used by the classification processor 20 and may load the binary tree data into the classification processor 20.

The example classification tree of FIG. 3 has no bearing on any real field of use, and is presented for instructional purposes only. Those skilled in the art will appreciate the particular analysis necessary in their field of use to classify events in that field, and will appreciate that their classification trees could look substantially different than the tree of FIG. 3.

Figure 5:
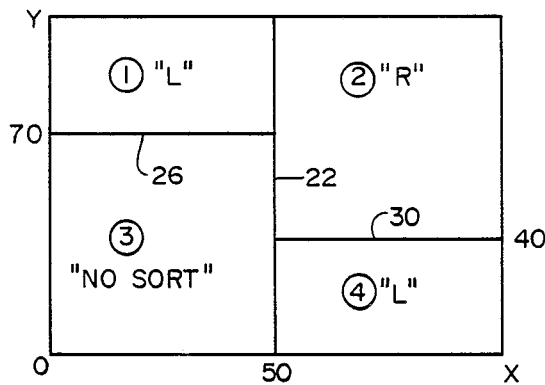
FIG. 5 is a diagram of the classifications of 4 different phenotypes based upon the binary decision tree of FIG. 3 as plotted in a two dimensional plane.

An example of how the process of FIG. 4 would be applied using the binary classification tree of FIG. 3 when implemented by the classification processor 20 follows, and reference is made to FIGS. 3 and 5. After an event is detected and the parameter data for it is generated, the classification processor 20 first inquires whether the x component of the two dimensional vector describing the event is greater than 50 at the node 41 of the tree. This is equivalent to drawing the line 22 in the plane of all possible two dimensional space events at the x value 50 in FIG. 5. If the answer to the question asked at node 21 is no, processing proceeds to the node 24 where the inquiry is whether the y component of the vector is greater than 70. This is equivalent to drawing the line 26 at the y value 70 in the universe of all possible events represented by FIG. 5. If the answer to the question in node 21 is yes, processing proceeds to the node 28 where the inquiry is whether the y component is greater than 40. This is equivalent to drawing the line 30 at the y value 40 in the universe of FIG. 5.

The result of making the comparisons of FIG. 5 is to classify all the events which have vectors or signatures with x and y components included within the universe represented by FIG. 5 into four different classifications labeled 1-4 in FIG. 5. If the events were cells dyed with fluorescent dyes attached passing before a laser beam and the x and y components of the vectors characterizing each cell were the forward scatter and the fluorescence value of each cell, the regions 1-4 would represent four different phenotypes. Each different phenotype would have a sorting decision associated with it stored in the classification processor's memory indicating whether it should sorted left, right or not at all as indicated in the rectangular regions of FIG. 5.

These sort decisions encoded in the binary tree would be supplied by a researcher who would have previously examined the vectors of data generated by the passage of an aliquot (a sample portion) of cells of the population to be sorted and made sort decisions based upon whatever method of analysis suited his or her needs. The data from the sample aliquot of cells would be transmitted to an analysis and tree generation system 38 via a bus 40. The user would then examine the cells in the sample and compare them to the vector generated for each cell. Based upon this analysis, the user could determine which cell types he or she is interested in and make a sort decision for each vector type. In the case of cells dyed with fluorescent dyes, each data vector representing a distinct phenotype would be assigned to a particular bin and a sort decision for that vector type assigned.

Returning to FIG. 1, the sort decision and data merge interface 111 serves to take the parameter data for each event from FIFO 15 via bus 113 and merge it with the associated sort decision from the classification processor 20 received via bus 115. The merged data is then sent to the user interface CPU 38 via bus 40 for display.

As an example of one type of classification routine which would work to perform the process shown in FIG. 4, please see the software listed below in the appendices.

Algorithms to perform classification on binary classification trees are well known and are described in numerous references. One such reference is Friedman, *Classification on Regression Trees*, Wadsworth International Group Publishing Co., Belmont, Calif. (1984), Library of Congress Call Number QA278.65.C54, ISBN 0-534-98053. Others are W. B. Jones, *Programming Concepts, A Second Course*, Prentice-Hall Inc. (1982), Library of Congress Call Number QA76.73.P2J66 ISBN 0-13-729970-2, E. Horowitz & S. Sahni, *Fundamentals or Computer Algorithms*, Computer Science Press (1978), Library of Congress Number ISBN 0-914894-22-6, and E. Horowitz & S. Sahni, *Fundamentals of Data Structures*, Computer Science Press (1983), Library of Congress Number ISBN 0-914894-20 all of which are incorporated by reference.

The sort decision FIFO buffer 34 in FIG. 1 serves to resynchronize the availability of the classification decisions with the need to take some classification action by the classification means 36 at the time 12. It will be understood by those skilled in the flow cytometry art that the time 12 corresponds to a location in the flow path of the cell containing stream. When the classification means 36 needs a classification decision for an object or event being acted upon at the time 12, it signals the FIFO buffer 34 via the signal line 44 to output the next classification decision. Of course the FIFO buffers assume the seriatim occurrence of events or arrival of signals or objects at the point 14 and the same occurrence order or arrival order at the point 12 albeit somewhat delayed in time.

In the field of cell sorting, the cells always arrive at the point 14 seriatim. Since the arrival order at the point 12 is the same as the arrival order at the point 14, FIFO buffers 18 for each channel and the sort decision FIFO 34 have the effect of synchronizing the system by their order of storage of data despite the fact that the amount of time the classification processor will need to traverse the classification tree is not always the same. For example, in cell sorting, it may be that 90% of the cells in a population can be eliminated by making comparisons at one or two nodes of the classification tree. These decisions would be made relatively fast. However to sort the desired phenotype which may represent say 5% of the total population out of the remaining 10% may require processing at every node level in the tree. Naturally, these decisions will be slower. The use of FIFO buffers at the input and output of the classification processor allows the classification processor freedom to spend the time it needs to properly classify all events without getting out of synchronization with the arrivals at the point 12 for action by the classification means.

The classification means 36 has a structure and function which is dependent upon the field of use of the invention. Those skilled in the art to which the invention is applied will appreciate the structure needed to convert the binary classification decisions arriving on the bus 46 to the proper set of actions for their particular field of use. In fields of use other than flow cytometry, the event stream 10 represents a stream of events separated in time.

In the field of cell sorting, the stream 10 represents a stream of cells entrained in a liquid stream which is being broken into tiny droplets by an ultrasonic transducer (not shown). In such a field of use, the classification means 36 consists of a known apparatus for receiving an event signal indicating that a cell has just passed the point 14 in the liquid stream, waiting a prescribed amount of time for the cell to travel in the stream 10 to the point 12 and for retrieving the classification decision from the sort decision FIFO buffer 34 and converting it to the proper polarity charging pulse to properly deflect the drop or drops containing the cell of interest into the proper container.

Referring to FIG. 7 there is shown a specific embodiment for a cell sorter using the invention. A nozzle 50 of known design guides a central stream of cell containing solution toward an orifice where the central stream is joined with a coaxial sheath stream of conductive fluid (not shown) as is well known in the prior art. A transducer 52 shakes the entire structure axially, i.e., parallel to the path of the stream, such that the stream breaks into tiny droplets, typically at the rate of 30,000 drops per second. A drop charging electrode is coupled to a DROP CHARGE signal 54 and is electrically coupled to the conductive sheath stream such that the drops have the charge on the line 54 at the time they break from the stream. The transducer 52 is driven by the DROP DRIVE signal on the line 56 from a sort control circuit to be discussed below.

The stream of liquid, before it breaks into drops, passes through two laser beams from the lasers 58 and 60. These two lasers have different wavelengths intended to be within the excitation bands of whatever fluorescent dyes which have been used to stain the cells in the stream. The laser light excites the dyes so as to cause fluorescence of the cells which have die molecules bound to them in a known manner. The dyes used depend upon the desired experiment, and the wavelengths of the lasers are well known and specified in the literature incorporated herein by reference.

The laser light hits the cells as they pass the two beams and scatters both forward and backward as is well known. Two scattered light detectors detect the forward scattered light and the wide angle scattered light typically. The selection and arrangement of these detectors is well known and in the incorporated literature, and will not be further detailed. Either photodiodes or photomultiplier tubes can be used for these scatter detectors.

The laser light also excites the dyes bound to certain of the cells and causes them to be fluorescent and emit light in the emission spectrum of each particular die that is excited. If a cell has 5 dye types bound to it, and all have excitation bands which cover the two laser frequencies, then 5 different emission spectra will exist in the emission bands of the 5 individual dyes because of the way the dyes are chosen. Some of these bands may slightly overlap each other, but generally each dye emits light of a different color. There are 5 different fluorescent light detectors which are designed to detect this fluorescent light in the preferred embodiment. There are also 3 scattered light detectors. These detectors and the two scattered light detectors are marked PMT 1 through PMT 8 in FIGS. 7A and 7B. Each detector is a photomultiplier tube, and each fluorescent light detector has a bandpass filter in front of it. These bandpass filters take the form of a colored filter which is selected to let light from only one band through to the photomultiplier. Each photomultiplier tube is supplied with high voltage from a programmable high voltage supply (now shown) the voltage of which may be individually adjusted by the user. The arrangement of these fluorescent light detectors relative to the stream and various beam splitters is well known and described in the literature incorporated herein.

Figure 7A:
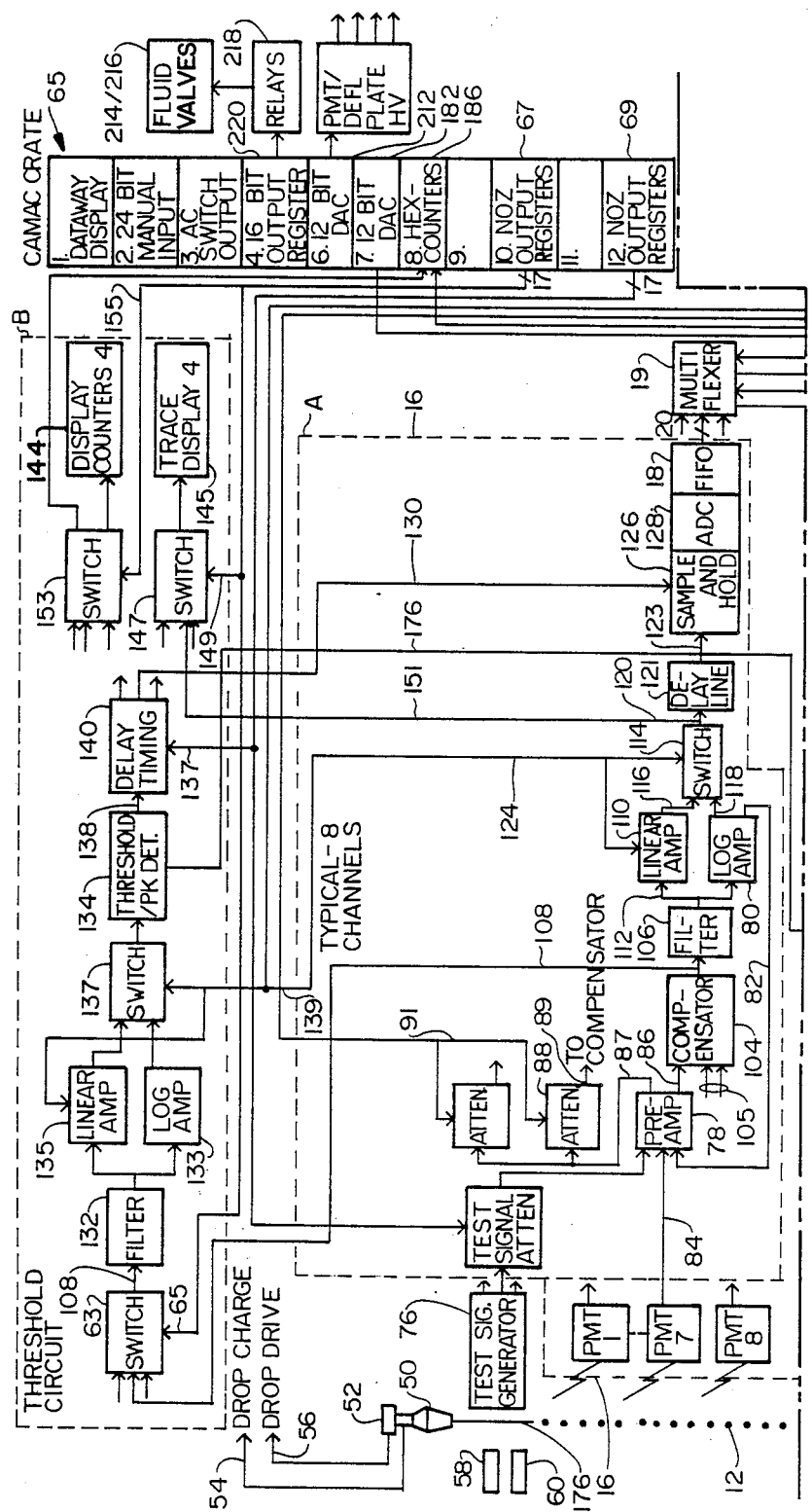
FIGS. 7A and 7B are a block diagram of the preferred embodiment of the real time classification system.
Figure 7B:
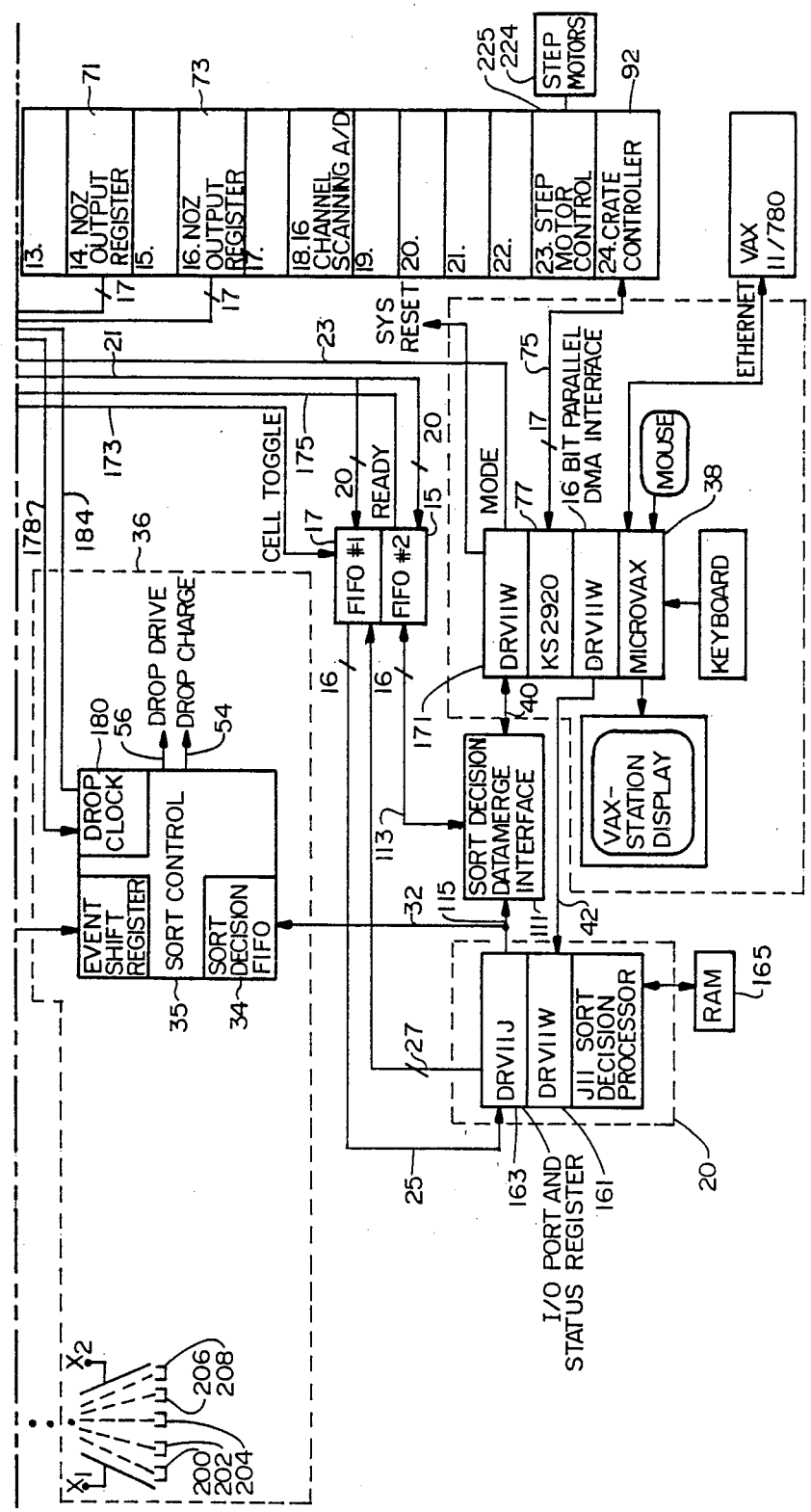

Thus 8 channels of signal information are present at the outputs of the 8 different light detectors. Each of these 8 different analog signal channels must be digitized, buffered and fed into a classification computer for comparison against a binary classification tree. Together, the 8 channels of information comprise an 8 component vector in 8 dimensional space. The job of digitizing and buffering the 8 channels of information is performed by 8 identical data channels. Only one data channel is illustrated in FIGS. 7A and 7B since all are of the same design. Each of the 8 channels has the design of the circuitry within the phantom line describing the box A connected to the output of the scatter detector 62.

In addition, all 8 data channels are served by additional event detection circuitry comprised of the circuitry within the box B which serves to detect the event of passage of a cell in front of the first laser. In the preferred embodiment, the event detection circuitry may be coupled to any of the photomultiplier tubes for event detection via a multiplexer 63. This multiplexer is under the control of the user via the control bus 65. The control bus 75 is shown as a solid line with a slash mark through the line labeled with a17 in FIG. 7 as are a number of other control buses coupling various circuits in the system to a CAMAC crate 65. The CAMAC crate is a commercially available modular instrumentation control system having a crate controller 92 coupled to a plurality commercially available circuits by a backplane bus (not shown). The purpose of the CAMAC crate is to control all the programmable devices in the system and provide various auxiliary functions to the gathering of data.

One of the circuit modules in the CAMAC crate 65 is an output register of which there are four designated 67, 69, 71 and 73. Each of these output registers is coupled by a 17 bit control bus indicated by a solid line with a slash through the line labeled with a 17 indicating the bus has 17 control lines to one or more circuits that are being controlled in the data channels A or the event detection circuitry B. Each 17 bit control bus is comprised of 12 data lines and 4 address lines plus a write strobe control line. Each of output registers 67, 69, 71 and 73 has 16 separately addressable registers (not shown) therein and a decoder (not shown) coupled to the address lines of the CAMAC crate 65. The decoder is coupled to the load control lines of the registers such that the CAMAC crate controller 92 can separately address and load data in or read data from any one of the 16 separately addressable data registers in each of the output registers 67, 69, 71 and 73. The output registers 67, 69, 71 and 73 also are structured such that appropriate address lines from the CAMAC crate 65 backplane bus that address the individual registers in each of the output registers such as register 67 are also coupled to the 4 address lines of the corresponding control bus. Each of the individual registers in one of the output registers 67, 69, 71 and 73 corresponds to one of the circuits in the system which is programmable by the user as to some aspect of its operation. The CAMAC crate controller 92 receives the data regarding how each circuit is to be controlled via a bus 75 from a KS2920 parallel CAMAC DMA interface circuit (available from Kinetic Systems) and the MICROVAX user interface CPU 38. This CPU runs the user interface software given in the appropriately labeled appendix to prompt the user to make the various choices available regarding how the system is to be set up. Once the choices are made, the set up data is communicated by the bus 75 to the CAMAC crate controller 92 which passes it along to the appropriate register in one of the output registers 67, 69, 71 and 73 which corresponds to the circuit being controlled. This is done by writing the address of the appropriate register on the CAMAC address bus and doing an I/O transaction to write the appropriate control data into the register. At the same time the register is loaded, the data with which it is loaded is placed on the data lines of the appropriated control bus such as the bus 65, and the address of the circuit being controlled is placed on the address lines of the same control bus. Each circuit being controlled in this manner has its own register to latch the data received in this manner. The address on the control bus enables the control register in the circuit being controlled to load the control data thereby establishing the electrical characteristics for that device that the user wishes the device to have.

The registers in the output registers 67, 69, 71, and 73 all store the same data that is stored in the circuits being controlled. The purpose of these registers in the output registers 67, 69, 71, and 73 is to enable the crate controller to read the status of any of the circuits being controlled without having to have all the wires and control signals necessary to do read and write transactions to a peripheral running out from the crate controller to all the devices being controlled.

The data channels A can be exercised for test purposes by injection of test signals from a test signal generator 76. Preferably this signal generator is capable of generating an analog signal having a gaussian distribution pulse shape which is similar to the pulse shapes of the pulses which each of the 8 photomultipliers output. It will be understood by those skilled in the art that not all of the 8 channels generate a pulse every time a cell passes in front of the first laser. This depends upon whether the cell has any dye bound to it. Further, the 8 detectors are split such that the three scatter detectors and three of the five fluorescence detectors are optically coupled to the first laser only, and the remaining two fluorescence detectors are optically coupled to the second laser which is down stream from the first laser as is known in the prior art. Thus the pulses from the first six detectors are separated in time from any pulses generated by the last two detectors by the amount of the travel time for a particular cell between the point the first laser beam strikes the stream and the point the second laser beam strikes the stream. For reasons that will be explained below, this difference in times of output of signals from the detectors for different channels is not a problem since the timing between event detection and sampling on each channel is independently controlled for each channel. This allows detection and data gathering from cells which are so closely spaced that 2 or 3 cells pass in front of the first laser before the first cell reaches the second laser. This means that the sensing stations can be spaced quite far apart without compromising the ability to track and classify closely spaced events. All prior art devices known to the inventors require a cell to pass in front of both lasers before the peak detect and sampling circuitry can be released to deal with another cell.

The analog pulse from each photomultiplier tube must be amplified, and preferably, the D.C. level of the background noise should be subtracted to improve the signal to noise ratio. This is the job of the preamplifier 78. Preamp 78 is a differential amplifier having its negative input coupled to the output of the photomultiplier tube 62 (or whatever light detector serves the particular channel) and having its positive input coupled to the output of a logarithmic amplifier 80 by a line 82. The logarithmic amplifier 80 includes an integrator (not shown) which is coupled to the line 82 which serves to integrate the average noise and feed the result back on the line 82 to the preamp 78. In this way, the average noise level is subtracted from the signal at the negative input on the line 84, and the difference is amplified and output on the line 86. The design for such a preamp and integrator are well known.

An attenuated version of the amplified signal on line 86 is coupled via line 87 to the input of a programmable attenuator 88 which serves to provide a compensation signal to compensate for cross talk between channels. The attenuator 88 generates an output signal on the line 89 which is a programmable fraction of the amplitude of the incoming signal on the line 87. The particular fraction which is output on line 89 is set by a user interface 38 or can be a constant. Preferably the user interface CPU prompts the user to specify the fraction and communicates it to a crate controller 92 in the CAMAC crate which then communicates it to the attenuator 88 in the manner described above via bus 91.

The MICROVAX in the user interface 38 serves to set up the machine parameters by communicating various gains, voltage levels and other parameters needed by the machine to control its operation via the CAMAC crate controller 92 and the bus 75. These parameters are set by the user. The attenuation value is written by the MICROVAX to the crate controller 92 via the bus 75 which then writes the constant into an output register 73 via a backplane bus (not shown) in the CAMAC crate. This output register is coupled to the attenuator 88 by a 17 bit bus 91. The structure of the CAMAC crate is well known and is available from several sources including LeCroy Research Systems Corporation of Spring Valley, N.Y. CAMAC crates are general purpose instrumentation racks with 25 slots connected to a backplane carrying power, data, address and control lines. The slots can be filled with various general purpose instrumentation support circuits such as output registers, I/O ports, counters, A/D converters, D/A converters, step motor controllers, memory cards, and a crate controller. These devices are available from numerous manufacturers. The devices in the CAMAC crate 65 of the invention are all commercially available. There follows a listing of the manufacturer and model number of each device in the CAMAC crate 65: All KS model numbers that follow are available from Kinectic Systems—Dataway Display KS3291; 24 Bit Manual Input KS3461; AC Switch Output KS3080; 16 Bit Output Register KS3076; 12 Bit D/A Converter KS3112; Hex Counters KS3610; NOZ Output Register available from Tom Nozaki of Stanford University Research Staff (design discussed above and detailed logic diagram included in appendices hereto); 16 Channel Scanning A/D converter (any CAMAC compatible converter will do).

The reason the attenuator 88 is desirable is that some of the dye emission spectra overlap. This means that one dye's emissions may cause signal output in more than one channel because some of its emitted fluorescent light has a frequency within the bandpass frequency of one of the other filters besides the filter intended to pass that particular dye's emissions. Because this is undesirable because of the cross talk interference between channels that it causes, compensation to subtract out the undesired components from each dye in channels other than the intended channel is needed. The programmable attenuator 88 does this. This attenuator is actually one or more attenuators depending upon how many other channels must be compensated for a particular dye's emission spectrum Each attenuator is assigned to compensate a particular channel's cross talk, and each attenuator has its own attenuation value assigned to it via the user interface 38, the crate controller 92, one of the NOZ output registers and a control bus like the bus 91. The user measures the amount of cross over noise in each channel by running only one dye type through the sorter and measuring the amount of cross over noise in each channel other than the one specifically designed to detect emissions from that particular dye.

In the preferred embodiment, the attenuator 88 is a digital to analog converter having a digital input coupled to the control bus 91 and having the analog input line 87 coupled to the D.C. reference voltage input, and having the analog output coupled to the line 89.

Compensation is accomplished by a differential amplifier compensator 104 having its positive input coupled to the line 86 and having its negative input coupled to the compensation lines 105 from the attenuators of all other channels which have cross over coupling of light into the particular channel involved. If more than one channel compensation input is connected to the negative input of the compensator 104, then the compensation inputs to this channel from all the other channels must be summed by known summing circuits prior to application to the negative input of the compensation amplifier 104. Generally, the compensation required will be between channels associated with the same laser. The sorter of FIGS. 7A and 7B is the first sorter known to the applicants wherein each channel may receive compensation signals from more than one channel, sum the compensation signals and use the composite signal for compensation purposes.

The output of the compensator 104 is coupled to the input of a filter 106 by a line 108. The filter 106 is present to improve the signal to noise ratio and timing of the system. Preferably it is a matched filter with its filter characteristic shape and bandwidth matched to the frequency spectrum and the shape of the frequency spectrum of the incoming pulse so as to maximize the signal to noise ratio. Of course all the circuitry such as the preamp 78, the compensator 104 and the attenuator 88 should have bandwidth, noise characteristics and linearity designed to pass many of the frequency components in the frequency spectrum of the input pulse, and not inject spurious noise or distort the input pulse. The input pulses from the light detectors have a generally gaussian distribution shape, and have a pulse duration on the order of 5 microseconds. A bandwidth of 250 kilohertz should be sufficient. The filter characteristic of a series of isolated RC stages each in a separate amplifier in a cascade of amplifiers has a generally gaussian distribution shape. The ideal matched filter characteristic curve for a gaussian shaped input pulse is also a gaussian shaped curve. Thus such a cascaded series of amplifiers approaches the characteristic of an ideal matched filter characteristic for a gaussian shaped input pulse, and will be sufficient for the filter 106 and the amplifiers preceding it.

The design of matched filters is well known, and the optimization of the filter 106 will be apparent to those skilled in the art from study of the literature and the treatise by Mischa Schwartz entitled *Information Transmission, Modulation, and Noise*, McGraw Hill Book Company, Inc., New York, N.Y. (1959), Library of Congress Catalog Card Number 59-9993 which is hereby incorporated by reference.

The output of the filter 106 is coupled to the inputs of a linear amplifier 110 and the logarithmic amplifier 80 by a line 112. The linear amplifier 110 is of conventional design, and the logarithmic amplifier has a transfer function designed to give a 5 decade dynamic range with an output increase of 2 volts in the range 0–10 volts for every decade increase in the amplitude of the input pulse. This logarithmic amplifier is commercially available from Tom Nozaki at the Stanford University Medical Center in Stanford, Calif. and the schematic diagram is available from him. The logarithmic amplifier is necessary because in measuring fluorescence, the input range of signals is very large. To be able to observe all sample cells on one range or scale is useful in this situation since extremely fine resolution is not needed. A relative change of 5%, if detectable, is sufficient resolution.

A switch 114 is coupled to the outputs of the logarithmic amplifier 80 and the linear amplifier 110 so as to be able to select which of the outputs on lines 116 and 118 will be coupled to an output line 120. The particular input line which is selected, is controlled by the user through the user interface 90, the crate controller 92 and an output register 71 coupled to a bus 124. That is, the user interface computer 38 can dictate which amplifier is selected by sending select data on the bus 124 via the crate controller 92 to the appropriate register in the output register 71 in the manner described above.

A delay line 121 is coupled to the output line 120 of the switch to impose a fixed delay on the input pulse before it reaches the circuitry which will sample it and digitize the sample. This fixed delay is an interval sufficient to delay the analog signal in each channel from appearing at the input of the sample and hold circuit 126 until a time after peak detection by the peak detector 134. The individual delay for each channel set in each of the delay timers 140 is then programmed to delay the pulse on line 138 for the corresponding channel and output it on line 130 for each channel at the time of the peak of the analog signal for that channel. The delayed input pulse appears on the line 123 for sampling.

The analog signal on the line 123 must be digitized. This is the function of a sample and hold circuit 126 and an A/D converter 128. The sample and hold circuit 126 serves to sample the analog value of the pulse on the line 123 at its peak and hold that value for use by the A/D converter 128. The sample and hold circuit 126 is conventional, and is signaled when to sample by a signal on a line 130. This signal comes from the delay timing shift register for the channel in question in circuit 140. The timing of the signal on line 130 is user programmable which results in the unexpected advantage that compensation may be achieved more accurately for the following reason. The shape of the event pulses may not be gaussian. Some zero crossings or other peculiarities in the shape of event pulses may result in compensation that is not perfect if the timing of the sampling by the sample and hold circuit 126 is not user programmable. In prior art devices, peak detection was used to determine when the sample the event pulse on any particular channel. This resulted in the problem that if, for example, channel 2 had cross coupling from channel 1 and no actual signal was supposed to result on channel 2 for a given situation, if a peak detector was used to control sampling and the shape of the compensation pulse was not the same as the shape of the erroneous "event" pulse on channel 2, a peak on channel 2 could occur when the correct channel 2 signal is zero. With programmable timing for the sample operation and programmable compensation levels, the sampling time in the above situation can be set for the maximum signal on channel 2 at a fixed compensation level, and the compensation level can be programmed to provide a zero output signal on channel 2 to get the correct result. Of course this same process is applicable to all the channels.

The sample and hold amplifier must have a sufficiently small acquisition time to capture the peak value for the particular pulse shape and duration of the events being detected.

The signal on line 130 also triggers a monostable multivibrator (not shown) to begin its timeout period. The timeout period is set so as to be long enough to allow the sample and hold acquisition time to pass. When the multivibrator times out, it generates a signal (not shown) which is coupled to the start conversion control input of the analog to digital to conversion circuit 128. Conversion is not actually started until an error status flag is checked.

The error status flag is a register (not shown) which is coupled to a control signal (not shown) from the FIFO 18. This control signal is activated when the FIFO 18 overflows. The FIFO 18 can store the data from only 16 events If all the space in the FIFO is used up, the control signal is activated to set the bit in the overflow register. Before the ADC 128 starts the conversion process, circuitry (not shown) checks this overflow register to see if there is room in the FIFO for the output data from the conversion. If there is room, the conversion is done. If there is no room, conversion is not done. The ADC 128 is coupled to the FIFO 18 by a 20 bit bus, and the FIFO 18 is coupled to the multiplexer 19 by a 20 bit bus. The overflow register is coupled to bit 15 of these buses. This allows dual FIFOs 15 and 17 to detect the overflow error. This will be described in more detail below.

There is also counter circuitry (not shown) in each channel to count the number of times that a conversion is performed. The count is then placed on bits 16, 17, 18 and 19 of the 20 bit bus to the FIFO 19 as the event identification data. Bits 12, 13 and 14 are hardwired for each channel to identify with each event's data, the channel number for that data.

The sampled value stored by the sample and hold circuit 126 is then converted to an 12 bit digital value by the A/D converter 128. This circuit is of conventional design. The sample and hold circuit 126 and the A/D converter 128 should be of a design which allows them to sample and convert two 5 microsecond duration pulses occurring one immediately following the other without loss of data or other distortion.

The timing of the sample and hold function is determined by the event detection circuit in the phantom box B. There is only one event detection circuit, and it serves to detect the occurrence of an event and to generate timing control signals for all the data channels. In the preferred embodiment, the event detection circuit is connected to the forward scatter channel. In other embodiments, the event detection circuit B could be coupled to any of the detector channels. In the preferred embodiment, the event detection circuit is connected to the first scatter channel because all objects the size of cells will generate scatter signals, but may not generate fluorescence signals that will be detected by the fluorescence channels. To allow the event detection circuit B to be connected to other channels, a programmable multiplexer 63 is used. This multiplexer has one input for each channel, and each input is coupled to the photomultiplier tube in the corresponding channel via the output of the compensation amplifier. The multiplexer has its control input coupled to the output register 67 via the control bus 65. The user can program the switch 63 to couple the photomultiplier tube of any channel to the event detection circuitry via the user interface computer 38.

The event detector B consists of a filter 132 having its input coupled to the output line 108 of the switch 63 so as to receive the pulse signals from the selected channel at the output of the compensation amplifier 104. The input of the filter 132 could also be connected to other parts of the circuit as well since it is only necessary that the circuit B detect the presence of a pulse. The filter 132 serves to filter out noise from outside the band of interest which encompasses the frequencies of the expected scatter pulses. The output of the filter 132 is connected to the input of a threshold circuit 134 via a logarithmic function amplifier 133 or a linear amplifier 135. The gain of the linear amplifier is programmable, and may be set by the user through the user interface computer 38 via the crate controller 92, and the output register 71.

Which of these two amplifiers 135 or 133 is selected to amplify the output of the filter 132 is controlled by a user programmable switch 137. This switch is controlled by the user interface computer 38 via the crate controller 92, the output register 71 and the control bus 139.

The output of the switch 137 is coupled to the threshold/peak detect circuit 134 which serves to block the passage of all signals which have less than a given threshold magnitude. This comparing of the incoming pulse magnitude to a minimum threshold prevents spurious timing signals from being generated from noise pulses. The threshold circuit 134 can be any known circuit capable of performing this function such as a comparator having one input coupled to a reference voltage coupled to a gate, or it may be a Schmitt trigger coupled to a gate to gate the pulse through to a peak detector. The threshold level is manually set, but in some embodiments it could be set via the user interface computer 38.

The output of the threshold circuit 134 is coupled to a peak detector which is shown as part of the block 134 in FIGS. 7A and 7B. The peak detector circuit serves to detect the time when the incoming pulse reaches its maximum amplitude and to generate an event signal on a line 138. This circuit can be any known device which performs the stated function. In the preferred embodiment, the peak detector is a differentiator which detects the change in slope of the input pulse from positive to negative and generates a signal which can be used to trigger a sample and hold circuit. This signal will cause the sample and hold amplifier in each channel like the circuit 126 in FIGS. 7A and 7B to sample the input pulse for that channel. This occurs after a suitable delay to account for travel time of the cell from the event detection point to the point where a particular data channel picks up a signal and that signal has had a chance to propagate to the sample and hold amplifier in question.

The signal on the line 138 from the output of the peak detector circuit is an indication that a cell has passed through the first laser beam in the embodiment shown in FIGS. 7A and 7B. This signal will be used to signal various portions of the circuit to start performing various functions. As noted above, one of these functions is to sample the analog signal on each channel and convert it to a digital value. However, since there is a slight propagation delay of the signal generated by the passage of a cell through a laser beam as the signal is propagated through the electronics between the detector and the A/D converter, a delay circuit 140 is used to compensate for the difference in the time of occurrence of the event and the time of arrival of the peak of the event pulse at the A/D converter.

The delay circuit 140 is comprised of a separate shift register for each data channel. The purpose of each shift register is to impose a user selectable delay for each channel between the time of event detection and the time that the signal in each channel is sampled. The length of the shift register and the resulting delay imposed by same is independently programmable for each channel via the control bus 137, output register 69 in the CAMAC crate and the user interface computer 38 and crate controller 92. This structure allows the detection and tracking of cells which are so closely spaced together that a second or third cell may pass through the event detection point before the first cell reaches the second laser. The independent delay for each channel used in the system shown in FIG. 7 allows the sensing stations or photomultipliers to be spaced quite far apart and changed at will without compromising the ability of the system to detect and classify closely spaced objects. When a change is made in the physical configuration of the system, the delay for each channel is altered to accommodate the change. The delay for each channel which is separately programmable along with FIFO storage for each event on each channel coupled with the synchronization circuitry to synchronize the collection of data from all the channels for a particular event eliminate the blind spot in the prior art. Further, the FIFO storage of sort decisions and resynchronization of the sort decisions with the arrival of the cells at the sorting apparatus gives great flexibility in the amount of time which is available to do any particular sort decision. All prior art devices currently known to the inventors require the cell to pass between both lasers before the peak detect and sampling circuitry can be freed to deal with another event.

The user can set the delay for each channel which is programmed into the delay timing circuit 140 empirically with the aid of a programmable trace display 145. This oscilloscope has 4 signal inputs and simultaneously displays 4 signals. The inputs are coupled through a multiplexer 147 to the signal paths of each of the 8 data channels at the output of the switch 114 in each channel. Line 142 is typical of one of these connections. The trace display 145 is also coupled to the outputs of the delay timing circuit 140 for each channel by connections not shown through the multiplexer 147. The multiplexer 147 is controlled by the control bus 149 through the output register 67 and the user interface computer 38 to select the particular channel for which the delay is to be set. When the switch 147 is programmed to connect the trace display 145 to a particular channel signal line such as 151, the corresponding output of the delay timing circuit 140 is also selected for display on the adjacent trace. This allows the user to graphically see when the pulse peak of the incoming data pulse occurs compared to the time when the corresponding sample signal to the sample and hold amplifier in the channel is issued from the delay timing circuit 140. If the input signal peak and the sample signal do not coincide, the user may alter the delay until they do coincide.

The delayed event signal from the delay circuit 140 is output on the line 130 to the sample input of the sample and hold circuit 126. The delay is set such that the event signal on the line 130 arrives at the same time as the peak of the pulse generated by that event arrives at the input of the sample and hold circuit 126 on the line 123.

There are also 4 display counters contained within the counter block 144. The counters 144 serve to count events. The input to the counters is controlled by a multiplexer 153 which is programmable via the user interface computer 38, the crate controller 92, the output register 67 and the control bus 155. The inputs to the multiplexer 153 may be coupled to any place in the circuitry of the various channels, but preferably are coupled to points in the individual channel circuitry to allow the counters to count the event pulses in each channel.

The output of the A/D converter 128 for each channel will be a digitized value indicative of the intensity of the fluorescent light emitted by a particular dye or the intensity of the scattered light depending upon which channel is considered. The output from the ADC 128 from each channel must be assembled into a vector in multi-dimensional space to serve as the signature of that particular event for sorting purposes.

This process of assembling the elements of each vector is done by the multiplexer 19 and the FIFO buffers 15 and 17 in addition to the FIFO buffer 18 in each channel. Each digitized value for an event is stored in the FIFO buffer 18 for that particular channel in the order of its arrival. That is, all the components of the multi-dimensional space vector for the first cell event will occupy the first positions in the FIFO buffers in the respective channels regardless of the arrival times of the individual component values at the buffers. By causing the FIFO 18 in each channel to output its first value, the multidimensional space vector for the first cell event can be read. Subsequent cell event vectors can be read by causing the FIFO's 18 in each channel to output their values in sequence. Each FIFO 18 generates a DATA READY output signal (not shown) on the bus connecting the FIFO to the multiplexer 19. This signal is active whenever the FIFO 18 for that particular channel is storing any data.

Reading of the elements of the multidimensional space vector from the FIFO buffers 18 in each channel by the multiplexer 19 is automatic once the mode is set by the user interface CPU 38. The mode is the channel numbers of the channels which will carry parameter data to be examined in a particular sort run. The mode data arrives on the bus 23 from the MICROVAX user interface computer 38. The multiplexer 19 has a mode mask comprised of a plurality of AND gates (not shown) and a comparator (not shown). One input of each AND gate is from the mode register and such that the bus comprised of all these inputs carries the bit pattern that defines the channels that are to be examined. The other input for each AND gate is coupled to the DATA READY output signal from the corresponding channel. When all the channel FIFO's 18 for the channels involved in any particular mode have activated their DATA READY signals, the comparator detects this fact and generates a signal which causes the multiplexer to start unloading the data from the FIFOs 18 and loading it into the FIFOs 15 and 17.

The multiplexer 19 has a scanner circuit therein (not shown) which is programmed with the channels that are to be used in any particular sort run by the data stored in the mode register (not shown). Programming of this scanner circuitry is by way of the user interface computer 38 and the DRV11WA I/O port 171 and the MODE control bus 23. The user may select the particular channels of interest for any particular sort run through the user interface software included herewith as an appendix. This software runs on the MICROVAX 38. The user may choose any of the 8 channels of data. Once the selection is made, the MICROVAX 38 does I/O operations to the I/O port 171 to write the mode data on the MODE control bus 23 into a register (not shown) in the multiplexer 19. The mode control data identifies which channels are to be read during the sort. The multiplexer 19 has its own clock and decoder circuitry which uses the mode control data in the register to automatically generate select signals to control switching of the various inputs of the multiplexer 19 to its output bus 21. The inputs of the multiplexer 19 are coupled to the outputs of the FIFO buffers 18 in each channel. If, for example, only channels 2, 3 and 5 are to be used on a particular sort, the multiplexer 19 controls its switching so that only the inputs coupled to channels 2, 3 and 5 are sequentially coupled to the output bus 21.

Thus, only elements 2, 3 and 5 of the multidimensional space vector for each event will be loaded into the FIFOs 15 and 17.

The FIFO's 16 and 17 can each store 16 multidimensional vector elements, i.e., 2 events if 8 vector elements are collected for each event. As soon as one element of an event vector is loaded, the FIFO's 15 and 17 each generate a control signal which serves to start the J11 classification process. The FIFO 17 activates a signal on the bus 25 which sets an event flag in a status register in an I/O port 163. In the preferred embodiment, the I/O port 163 is a DEC DRV11J. When the classification processor polls this event flag and finds it set, the J11 processor 20 vectors to a routine which does an I/O read of the FIFO 17 to obtain the values of the vector in multidimensional space symbolizing the event's characteristics. The scanning multiplexer 19 has the ability to unload 8 parameters or elements values from the FIFO's 18 in all 8 channels in 4 microseconds. This is much faster than the J11 sort decision processor can sense that the event flag is set and perform the necessary I/O operations to obtain the data to make the classification decision. Thus, all the elements of the vector will have been loaded into the FIFO buffer 17 before the J11 sort decision processor 20 needs this data. The FIFO 15 will generate a control signal on the bus 113 as soon as the first element is loaded therein to signal the sort decision/data merge interface 111 that data is available in the FIFO 15 for merging with the sort decision as soon as the J11 sort decision processor 20 makes the sort decision. The sort decision processor 20 will send the sort decision to the interface circuit 111 via a bus 115. This decision data will be merged with the raw data itself from the FIFO 15 received on a bus 113 by the interface circuit 111. The combined data will be sent to the MICROVAX user interface computer for display via the bus 40.

The typical event pulse width is 5 microseconds. The conversion time to convert the pulse peak to a digital value is 2 microseconds and the acquisition time to sample and hold the analog value of the peak is 1 microsecond. The typical travel time for a cell to travel from a position in front of the first laser to a position in front of the second laser is 15 microseconds. Thus several events or cells may have passed before the first laser before the first one in the group passed before the second laser. This is why the individual delay shift registers for each channel are important because such a structure allows the data from closely spaced events to be processed rather than missed as would occur in the prior art systems. Each of the FIFO's 18 can store data from up to 16 events, and the typical worse case for the time it takes to make a classification decision is such that the FIFO's 18 will have more than one or more events stored only one fourth of the time.

The data unloaded from the FIFO 15 will be stored in a register in the I/O port 163. The J11 sort decision processor then performs the sort decision according to the process shown in FIG. 4.

The FIFOs 15 and 17 include, in addition to the FIFO storage circuitry, circuitry (not shown) to look for three different types of error conditions and switching circuitry to control three bits on the 16 bit buses 25 and 113 to identify these errors. The three types of errors that are looked for are: (1) does the channel number on the 20 bit input bus 21 for each parameter "word" match the expected channel number; (2) does the cell identification number for the parameter for each channel's data match for data from the same cell event; and, (3)) has there been an overflow of FIFO 18. These errors are screened by examining the cell identification data on bits 16, 17, 18 and 19 and by examining the buffer identification data on bits 12, 13 and 14 of the 20 bit bus 21. The multiplexer 19 includes circuitry (not shown) which generates a control signal CELL TOGGLE on a control line 173 which changes states each time all the data for a particular mode has been output to the dual FIFOs 15 and 17. This signal is used as a marker to delimit between cells.

The FIFOs 17 and 15 must reduce the 20 bits of data on the bus 21 down to 16 bits of data on the buses 25 and 113. Of the 16 bits on these two buses, 12 bits are data, bits 12, 13 and 14 may be either the type of error that occurred or the channel number data, under software control, and bit 15 is an "or" of the three errors. The FIFOs 15 and 17 store the type of error which occurred, if any, in an internal register (not shown). There is switching circuitry (not shown) which alternately couples either this register or the incoming bits 12, 13 and 14 from bus 21 to bits 12, 13 and 14 of the buses 25 and 113 depending upon control signals received from either the J11 classification processor 20 or the MICROVAX 38. These control signals take the form of two bits in the output registers of the DRV11J I/O port 163 of the J11 or the DRV11WA I/O port 171 of the MICROVAX. These bits, 13 and 14, are under software control and are coupled from the MICROVAX 38 to the dual FIFOs via bus 40, datamerge interface 111 and the bus 113. These two bits are communicated from the J11 I/O port output register via a bus 27. If either computer sets bit 13, this means the computer is requesting status which means that the dual FIFOs 15 and 17 are supposed to put either the buffer ID or the type of error on bits 12–14 of the output buses 25 and/or 113. The state of bit 14 indicates whether the channel ID or the type of error is being requested. These two bits control the switching action by the multiplexer circuitry which controls the contents of bits 12, 13 and 14 of the buses 25 and 113.

The J11 classification processor 20 and the MICROVAX user interface computer 38 each may override the operations of the other. This means for example, that when the J11 overrides the MICROVAX, only sort decisions are made, and the data from the datamerge interface 111 is not displayed by the MICROVAX. If the MICROVAX overrides the J11, the data from the sorter on the bus 40 is only displayed by the MICROVAX and no sort decisions are made on the data collected by the channels. This override function is under software control. Two bits in the output registers 171 and 163 are dedicated to this function. These bits cause control circuitry (not shown) in the FIFOs 15 and 17 to generate a READY signal at the appropriate time on signal line 175 to indicate to the multiplexer 19 when data may be placed on the bus 21. If the MICROVAX has been overridden, the READY signal will be made active when FIFO 17 is ready to accept data regardless of the status of the FIFO 15. If the J11 has been overridden, the READY signal will be activated as soon as the FIFO 15 is ready to accept data regardless of the status of the FIFO 17. If neither computer is overridden, the READY signal will not be activated until both FIFOs 15 and 17 are ready to accept new data.

The J11 classification processor 94 is a Digital Equipment Corporation KDJ-11 11/73 minicomputer in the preferred embodiment. The J11 classification processor 20 receives the data needed to define the binary classification tree and to specify the values at the nodes of the classification tree from the user interface 90 through the DRV11WA DMA Interface 161. The same data path is used by the user interface processor 38 to down load the mode data to the J11 classification processor 20. The J11 classification processor sequentially accesses all the parameter data or elements of the vector in multidimensional space for a single event from the FIFO 17 and places all this data in RAM 165. The appropriated element needed to process at the first node in the classification tree is then retrieved from RAM 165, and the data is retrieved thereafter in the order dictated by the particular path taken by the J11 classification processor through the binary classification tree.

After performing the classification task by comparing the incoming data against the nodes of a classification tree such as the tree of FIG. 5, the sort decision is made by the J11 sort decision processor 20. This sort decision is encoded in a data word and sent on a bus 32 from the I/O port 163 to a sort decision FIFO buffer 34 in a sort control apparatus 36. The sort decision FIFO buffer 34 stacks the sort decisions to await the arrival of the cells to which each sort decision applies at the drop break off point 176. The sort control apparatus 36 delays implementation of the sort decision by an amount of time which can be set by the user by adjusting a control on the sort control circuit based upon the time delay found to work best in sample sorting. The sort control FIFO buffer 34 allows the J11 classification processor 20 to take as long as it needs on the more time consuming classifications (within limits) without losing synchronization with arrival of cells at the drop break off point. Most classifications can be done in a very short time, and these decisions are made and stored so that there is more time to make the more difficult classification decisions. The time limit on the decisional process is thus more flexible by virtue of the presence of the FIFO buffers 18, 15, 17 and 34 in the circuit, with the limits being that the classification decision must be made, and the decision stored in the sort decision FIFO buffer 34 before the cell to which the decision pertains arrives at the drop break off point 176. After the drop breaks off from the stream, it can no longer be charged by the DROP CHARGE signal on line 54, so no sorting action can occur for this drop if the drop must be charged to implement the sort decision once the drop breaks from the conductive stream.

The function of the sort control apparatus 36 is to implement the sort control decisions stored in the sort decision FIFO buffer 34 by properly charging the drop or drops assigned to each cell to which a particular sort decision pertains. The structure of the sort control circuitry 35 is well known for two way sorting, and only a few modifications are needed to adapt this known sort control to a four way sort. The sort control circuit 35 senses the occurrence of an event by monitoring a line 176 coupled to the peak detector 134. This signal on line 176 marks the time the cell appears before the first laser.

The designs for all the electronics in the data channels and the event detection circuitry inside the box B is given in the circuitry of Appendix A not printed in the Letters Patent but retained in the Patent File Wrapper. The details of these schematics will be understood by those skilled in the art given the high level discussion herein of what each functional block does and how it relates to the other circuits in the system given herein. Further, suitable designs can be derived from the following treatises which are hereby incorporated by reference:

Graeme, Jerald G., et al., eds. *Operational Amplifiers: Design and Applications*. New York: McGraw-Hill, 1971. LC Card No. 74-163297. ISBN 07-064917-0.

Artwick, Bruce A. *Microcomputer Interfacing*. Englewood Cliffs, N.J.: Prentice-Hall, 1980. LC Card No. 79-16747. ISBN 0-13-580902-9.

Seidman, Arthur H., ed. *Integrated Circuits Applications Handbook*. New York: John Wiley & Sons, 1983. LC Card No. 82-10903. ISBN 0-471-07765-8.

Millman, Jacob. *Microelectronics: Digital and Analog Circuits and Systems*. New York: McGraw-Hill, 1979. LC Card No. 78-8552. ISBN 0-07-042327-X.

Millman, Jacob, and Herbert Taub. *Pulse, Digital, and Switching Waveforms*. New York: McGraw-Hill, 1965. LC Card No. 64-66293. ISBN 07-042386-5.

Millman, Jacob, and Christos C. Halkias. *Electronic Devices and Circuits*. New York: McGraw-Hill, 1967. LC Card No. 67-16934.

Fink, Donald G., and Donald Christiansen, *Electronics Engineer's Handbook*. New York: McGraw-Hill, 1982. LC Card No. 81-3756. ISBN 0-07-020981-2.

The various software programs that control the system are given in the appendices B through J not printed in the Letters'Patent but retained in the Patent File Wrapper. Appendix B is the ROM program run by the J11 classification processor to process data using the binary classification tree to make sort decisions, also including the routines which interface with the DRV11J and the program run by the MICROVAX to download the binary classification tree data. Appendix C is the program which the MICROVAX runs to implement the user interface. Appendix D is the XA driver program that the MICROVAX runs to download the binary classification tree data. Appendix E is the SUP device driver for the datamerge interface circuit to collect sort data for display on the MICROVAX. Appendix F is the CA driver program that allows the MICROVAX to drive the CAMAC crate. This program is commercially available from Kinetic Systems and comes with the CAMAC crate. Appendix G is the Kinetic Systems "online" program which is run by the MIRCROVAX at powerup to initialize the CAMAC crate and deinhibit it. This utility also comes with the CAMAC crate.

Figure 8A:
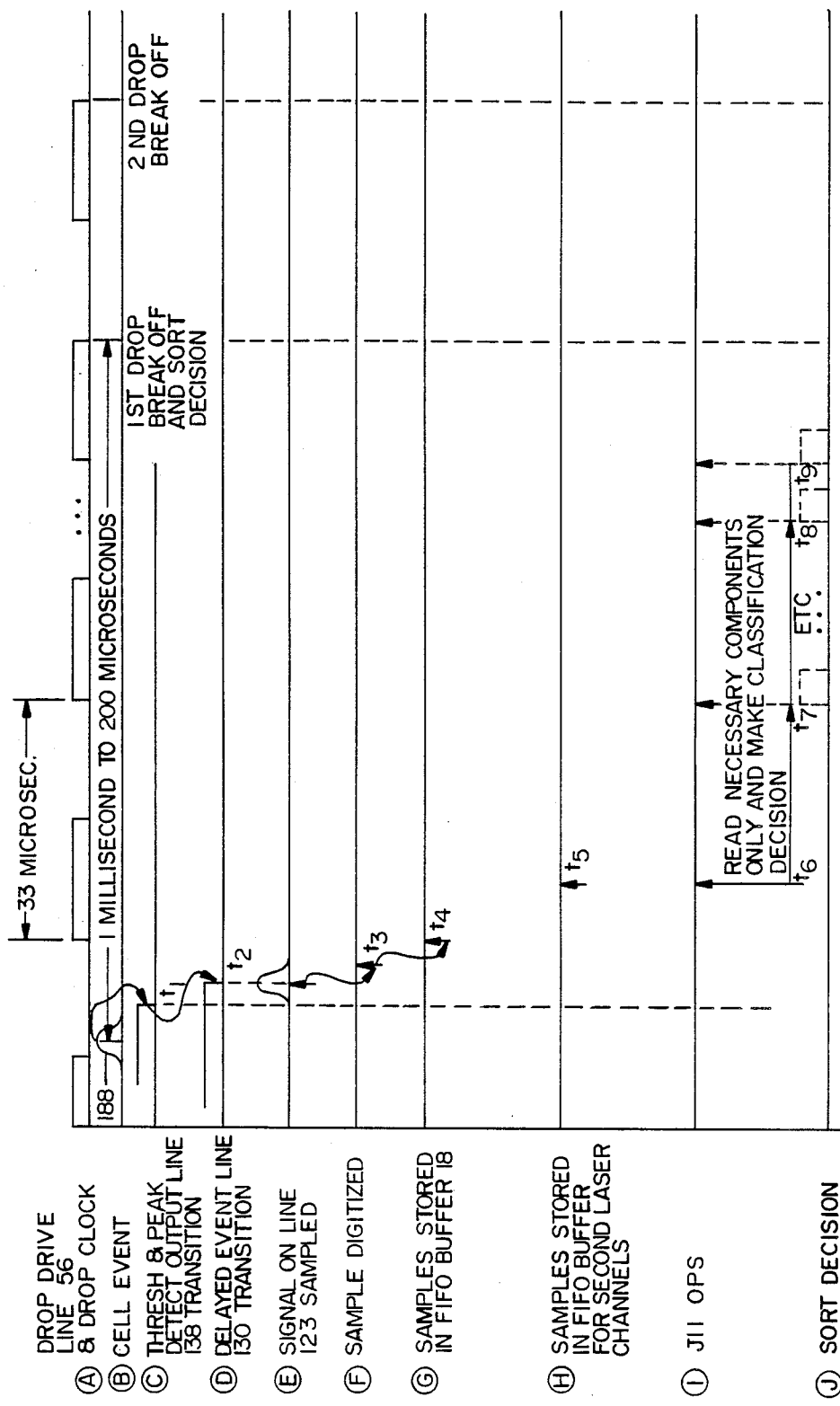
FIGS. 8A and 8B are a timing diagram of the operation of the apparatus of FIGS. 7A and 7B.
Figure 8B:
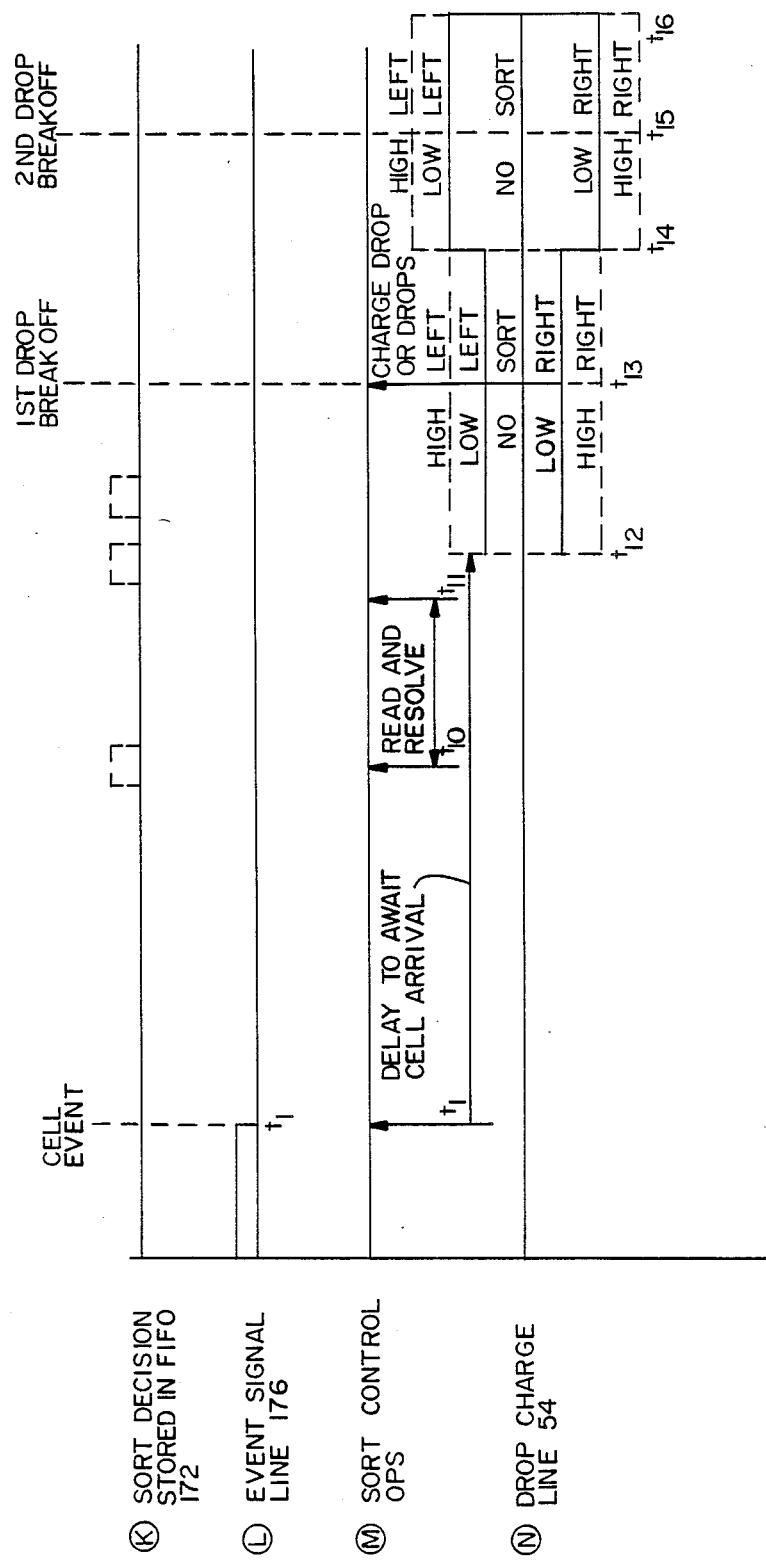

The timing of the various events in the machine, and of the sort control events is illustrated in FIG. 8A and 8B. The function of the sort control will be best understood by reference to these figures. The particular signal or event detailed on each of the lettered lines is identified by its signal line or function in the left margin, and the relative timing of the various events is indicated by the relative left to right spacing of the event indicator pulse or arrow with time increasing to the right.

Line A indicates the frequency at which drops are formed. They are formed at the frequency of the DROP DRIVE signal on the drop drive line 56 driving the transducer 52. The transducter 52 shakes the nozzle thereby causing drop break off. Drop formation occurs at a programmable rate, which depends upon the size of the nozzle. In the preferred embodiment, 30,000 drops per second are formed. This drop formation rate corresponds to a 30 kilohertz drop drive frequency. Thus a drop is formed about every 33 microseconds. The drop drive line 56 has a signal frequency which is set by the signal on the line 178 to a drop clock 180. The drop formation frequency is set by a digital value sent by the user interface computer 38 to a D/A converter 182 via the crate controller 92. The drop formation rate is counted by a counter 186 which reads the frequency of the drop clock 180 through the line 184. The drop counter 186 also includes circuitry to correct for drift in the drop formation rate by sending different digital data to the digital to analog converter 182 to cause it to adjust the analog signal on line 178 to change the frequency of the DROP DRIVE signal on line 56.

Cell events where a cell passes in front of a laser beam occur randomly and are indicated schematically by the gaussian shaped pulse 188. The peak of this pulse causes the transition at time t1 as shown on line C. This transition occurs on the signal line 138 in FIGS. 7A and 7B. The delay imposed by the delay timing circuit 140 delays the transition on the line 130 until the time t2 as shown on line D for each channel where the interval between times t1 and t2 is user programmable as previously described. For simplicity, only the events from one channel are shown in FIGS. 8A and 8B. At time t2, the pulse on the signal line 123 in FIGS. 7A and 7B is sampled, and this sample is digitized by the time t3 which is about 3 microseconds later. The digitized data is stored at the time t4 in the FIFO buffer 18. The time t4 may be different for each channel if the programmable delay programmed by the user into the corresponding shift register in delay timing circuit 140 in FIGS. 7A and 7B is different from the timing shown in FIG. 8A. A similar chain of events occurs on all the channels coupled to the laser beam of the second laser except some of the events will occur later in time by an interval equal to the travel time for the cell to the position of the second laser beam. These events are not shown to avoid repetition except for the storage time for the digitized data in the FIFO buffers for these channels at the time t5. Of course, the times t5 are also individualized for the second laser channels based upon the delay programmed into the delay timing circuitry 140 in FIGS. 7A and 7B for these channels.

The J11 processor 94 can begin its classification process at any time after time t5 for the first cell event stored in the FIFO buffers 18 of each channel. The J11 classification processor 20 can essentially run asynchronously reading data out of the FIFO buffers 18 after time t5. Each FIFO buffer 18 also includes circuitry to generate and store the channel number of the event data, i.e., the element number or dimension of the data in the multidimensional space vector characterizing the event. This element number data is stored along with the data and the event. The J11 classification processor 20 polls the event flag in I/O port 163 until the FIFO buffer 17 in FIGS. 7A and 7B indicates that some data has arrived.

The J11 makes the sort decision on the first cell event sometime during the interval between the times t6 and t9. The particular time needed depends upon the closeness of the event signature to the desired phenotypes, and the number of levels of the classification tree which must be traversed to make the decision. This varying amount of decision time is illustrated schematically by the illustration of three exemplary decision times indicated in phantom on line I of FIG. 8A. As each sort decision is made, it is reported on the bus 32/115 as indicated on line J. These sort decisions are stored in the FIFO 34 as they arrive as shown on line K.

The sort control circuit 35 is first signaled regarding the occurrence of an event when a transition occurs on the line 176 at time t1 as indicated at line L of FIG. 8A.

Several functions are performed by the sort control circuit 35. Chief among them is to convert the sort decisions stored in the FIFO 34 to the proper polarity drop charging pulse and output this drop charging pulse as the DROP CHARGE signal on line 54. Other functions are conflict resolution where two cells having different sort classifications break off in the same drop or two adjacent drops. This conflict problem and its resolution is well known as is the circuitry to resolve the conflict. Another function of the sort control circuit 35 is to insure the drop break off times are in the middle of the drop charging pulses for those drops. Another function of the sort control circuit is to assign one or two drops to each cell depending upon information from the user interface 38, and to apply a higher drop charging pulse to the second drop assigned to the same cell if two drop sorting is used. The reason for this is known and has to do with the electrostatic repulsion of the second drop by the charge placed on the first drop.

The main function of implementing the sort decision and generation of a drop charging pulse requires delay circuitry in the sort control circuit 35 to wait an adjustable amount of time from the time of receipt of a cell event signal on the line 176 until generation of the drop charging pulse. This time is illustrated on line M as the time between time t1 and t12. The sort control may do this by counting the number of drop break off points in the drop drive waveform until the delay period has passed, and starting the drop charge pulse at a time just before the drop break off point t13 for the first drop assigned to a particular cell such that the drop break off point occurs at the middle of the drop charging pulse. During this delay period, the sort control reads the sort decision out of the FIFO buffer at a time t10 and resolves any conflicts that exist if two cell events with different sort decisions occurred within the period of time assigned to one drop. The time between t10 and t11 is reserved for resolving any conflicts that exist. The conflict resolution algorithm and circuitry are known, and such apparatus are incorporated in the sort control circuitry 35. Such circuitry is commercially available. The J11 can make separate sort decisions for two events which occur very close in time, as long as the electronics are able to resolve the two events into separate multidimensional space vectors The drop charging pulse starts at time t12, and can assume one of five voltages: high left meaning the highest voltage for a left sort into the leftmost bin 200; low left meaning the lower voltage needed to deflect a drop into the bin 202; no sort which means the voltage needed to guide the drop into the bin 204; low right meaning the voltage needed to guide the drop into the bin 206; and high right meaning the voltage needed to guide the drop into the bin 208. The fine tuning of the deflection trajectories can be done by the user by adjusting the voltage on the deflection plates coupled to the high voltage supply 74 by the lines X1 and X2. As can be seen from inspection of the drop charging signal between the times t14 and t16, the voltages increase and decrease for the various sort classifications to compensate for electrostatic repulsion or attraction. The second drop break off point is t15 in the middle of the second drop charging pulse.

Various peripheral functions are also controlled through the user interface and the CAMAC crate such as monitoring various fluid levels through the sensors and A/D converters 212. Also the various fluid flows in the system can be started and stopped through the solenoid operated valves 214 and 216 and the relays 218 by sending the proper bits to the separate output registers in card 220 assigned to the addresses of the solenoid valves. These bits control the switch positions of the relays 218 which apply power or cut power to or from the solenoids. Digitally controlled step motors 224 can be controlled through card 225 by sending the proper bytes indicating the desired command, the desired location, the run rate, jog rate, acceleration rate and so on to define the velocity profile and the desired displacement. The step motors can be used to move a glass slide under the stream to capture single cells at different points on the surface of the slide in a known manner or to adjust and maintain the laser or other optical alignment.

There are several software appendices B through J not printed in the Letters Patent but retained in the Patent File Wrapper. Appendix B is the code the J11 classification processor runs to compare the data collected by the various channels to the binary classification tree node values to arrive at a sort decision. Appendix C is the driver routine for the DRV11WA interface I/O port between the MICROVAX and the sorter apparatus. Appendix D is the code that allows the J11 classification processor to communicate with the MICROVAX and vice versa. This code is a driver for the DRV11A which is called when the code of Appendix J is run. This occurs when the MICROVAX downloads the data defining a binary classification tree into the J11. Appendix E is the code the MICROVAX runs to display the sort data in pairs in two dimensional windows. Appendix F is the CAMAC crate driver code which is run by the MICROVAX when data is to be sent to the CAMAC crate. Appendix G is the code run by the MICROVAX to implement the user interface to prompt the user for parameters to control the sorting actions and signal processing actions of the sorting apparatus and to communicate user choices for parameters to various elements of the machine to establish operating conditions. Appendix H is the code run by the J11 after a system reset. This code dumps the data currently being worked upon by the J11 and ignores the next value read. Thereafter, the data which is collected is used to make simple classification decisions based upon whether the data is greater or less than one half scale. Appendix I is the code run by the MICROVAX upon powerup to initialize and deinhibit the CAMAC crate. Appendix J is the code which is run by the MICROVAX to send the data which defines a binary classification tree to the J11. The driver of Appendix D is called to aid in this function.

Although the invention has been described in terms of the preferred embodiment, those skilled in the art will appreciate many variations which may be made without departing from the true spirit and scope of the invention. All such variations are intended to be included within the scope of the claims appended hereto.

What is claimed is:

1. An apparatus for making classification decisions in real time comprising:
    means for gathering and buffering digital data in multidimensional space having greater than three dimensions describing the characteristics of one or more events including FIFO storage means for storing said digital data in first-in-first-out order along with an event number for use in correlating said data from each said dimension from the same event; and means for comparing selectable dimensions of said data in real time to a binary classification tree and for making a classification decision in real time based upon said comparison; and means coupled to said means for comparing for receiving and storing said classification decision until such time as an event is to be sorted and then for using said classification decision to sort the event in real time to which said classification decision applies into the proper category.

2. An apparatus for making classification decisions in real time on events and sorting in real time said events based upon said classification decisions comprising:

means for asynchronously collecting multidimensional data about an event through a plurality of sensors providing analog signals at analog signal outputs, each said analog signal from one of said sensors having a peak for the corresponding event, said multidimensional data defining a space having more than three dimensions, each said analog signal output being coupled to an input of a corresponding channel means, each said channel means including means for sampling the corresponding analog signal and converting said corresponding analog signal to a digital data sample, each said channel means having a separate means for sampling each said analog signal corresponding to an event at the peak of said analog signal corresponding to said event and for converting each said sample to a digital data sample;

first means for temporarily storing said digital data samples in a FIFO buffer along with data by which data samples corresponding to any particular event may be correlated to that event, and where said FIFO buffer includes a separate FIFO buffer for each said channel means, said FIFO buffer storing said digital data samples in first-in-first-out fashion, and wherein each said separate FIFO buffer includes means to generate a control signal when data is present in said separate FIFO buffer;

means for synchronizing the access of all said digital data samples which pertain to a particular event by retrieving said data from said FIFO buffer when said control signal indicates that data from selectable ones of said channel means is present in all the FIFO buffers for the selected channels, and for comparing in real time said digital data samples so accessed to the node values of a binary classification decision tree and for generating classification decision data in real time based upon said comparisons;

second means for temporarily storing said classification decisions for a predetermined time; and sorting means for retrieving from said second means the classification decision pertaining to each event at a predetermined time and for sorting said event based upon the classification decision pertaining to said event.

3. The apparatus of claim 2 further comprising event detection means for detecting when an event occurs and for generating an event signal, and further comprising an individual, programmable delay means corresponding to each said channel means for receiving said event signal and for delaying it by a programmable amount and then generating a sample signal and transmitting it to said means for sampling to cause said means for sampling to sample said analog signal.

4. The apparatus of claim 3 further comprising attenuation means in each channel means for attenuating the analog signal in each channel by a programmable amount and for outputting said attenuated analog signal as a compensation signal, and further comprising compensation means in each said channel means for receiving said compensation signals from predetermined ones of said other channels and for summing the compensation signals and decreasing the analog signal in the channel of interest by an amount proportional to the sum of said compensation signals.

5. A cell-sorting decision-making apparatus comprising:

a laser for generating a light beam;

a plurality of scattered light and fluorescent light detectors;

nozzle means for causing a stream of conductive liquid in which have been entrained a plurality of cells to which fluorescing dye has been attached to flow through said light beam, said cells to be sorted after they pass through the beam of said laser and for causing said stream to break into a plurality of droplets containing said cells to be sorted;

means for sensing when a cell has passed through said laser beam and for generating a first signal indicating the time of said passage for each said cell so detected;

means for receiving said first signal for each cell so detected and for generating a second signal in response to said first signal, each said second signal being delayed by a programmable amount from the time of occurrence of said first signal;

a plurality of channel means, each coupled to one of said scattered light or fluorescent light detectors, each said channel means comprising means for sampling and digitizing the analog signal generated by the corresponding detector as a cell passes through said laser beam, and each said channel means further comprising attenuation means for generating a compensation signal which is an attenuated copy of the signal being sampled by said channel means wherein said attenuation means is programmable, and each said channel means further comprising compensation means for receiving said compensation signals from selected ones of said other channel means and for compensating the signal being sampled for crosstalk between said channel means which could generated errors, said means for sampling and digitizing further comprising sampling means for receiving a corresponding one of said second signals for each event defined as a cell passing through said light beam passage of said cell through said light beam being detected and for sampling the analog signal generated by the corresponding one of said light detectors caused by each said event at the time of receipt of the corresponding one of said second signals, and, said means for sampling and digitizing further comprising digitizing means for converting the samples analog signal from said corresponding light detector to a digital value representing one characteristic of said event;

a FIFO storage means coupled to each said channel means for asynchronously receiving said digital value corresponding to said one characteristic of each event detected by the light detector coupled to said corresponding channel means and for storing said digital data in first-in-first-out order;

means in said plurality of channel means to generate a third signal when an event has been detected and for storing said third signal in said FIFO storage means with said digital data characterizing the event which caused the generation of said third signal, said third signal including event number data and channel number data;

means for receiving said third signal from each said FIFO storage means and for comparing said third signal to sort mode data supplied from an external source indicating which channels are involved in a particular sort mode, and when said third signal has been received from each said FIFO storage means for all the channels involved in a particular sort mode, for sequentially reading the digital values from only the FIFO storage means for the channels involved in a particular sort mode and outputting said digital values on a bus;

second FIFO means for receiving and storing the digital data from said means for receiving said third signal;

classification means for reading the data from said second FIFO means and for comparing the digital values representing all the characteristics of an event that were gathered for the current sort mode and for comparing said data to the nodes of a binary classification tree and for traversing through said binary classification tree on a path based upon the results of said comparisons and for making a sort decision based upon the path taken through said binary classification tree.

6. The apparatus of claim 5 further comprising:

sort means for receiving said sort decisions from said classification means and for generating a drop charge signal and further comprising means to couple said drop charge signal to said conductive stream for charging the conductive stream to a potential related to the sort decision and for electrostatically deflecting said droplets into a bin corresponding to said sort decision.

7. The apparatus of claim 5 further comprising means for loading binary classification tree data into said classification means.

8. The apparatus of claim 7 further comprising means coupled to said multiplexer means and to said classification means for merging the digital values representing the characteristics of a particular cell with the sort decision corresponding to said cell and for displaying said digital values on one or more two dimensional displays.

9. The apparatus of claim 8 further comprising user interface means for prompting the user to enter parameters to control the operation of said apparatus for making sort decisions such as the amount of attenuation to set on each channel to generate said compensation signal and the amount of delay between said first signal and each corresponding second signal, and for generating control data to control said apparatus for making sort decisions in accordance with the parameters entered by said user.

10. A method of sorting objects comprising the steps of:

gathering light scatter and fluorescence data in a multidimensional space having more than three dimensions by passing said objects through one or more laser beams and collecting scattered and fluorescent light using a plurality of detectors and an event detector coupled to one of said detectors to generate an event signal and a plurality of signal conditioning channels, each said channel including a sample and hold circuit and a FIFO buffer, with each said channel coupled to one of said detectors, by generating a sample signal using said event detector and delaying said sample signal a selectable delay interval for each said channel, the amount of delay for each channel being selected to correspond to the time delay from the time an event is detected at the detector to which said event detector is coupled to the time when the signal peak occurs in the signal corresponding to the same event as detected by a detector coupled to that channel, and for coupling said peak in said signal using said sample and hold circuit as triggered by said delayed sample signal, and converting the sampled signal value to digital data, and storing all said digital data corresponding to a particular event in the same relative position in all said FIFO buffers in said plurality of channels along with data indicating the event to which each piece of digital data in said FIFO buffers corresponds;

resynchronizing all said digital data corresponding to a particular event by retrieving all said data corresponding to a particular event from the same relative locations in said FIFO buffers and comparing said light scatter and fluorescence data in real time to a binary classification tree having node values which define the various classes of events to be separated and making a sort decision in real time regarding substantially all events; and using said sort decisions to sort said objects in real time.

11. A method of processing data elements describing a plurality of characteristics of a plurality of events for purposes of sorting said events into classes comprising the steps of:

asynchronously gathering a plurality of data elements regarding a plurality of different characteristics of each of a plurality of different events to be sorted using a plurality of different channels of signal processing circuitry where each channel gathers data elements regarding one characteristic of each event to be sorted by sampling a signal corresponding to said event when the peak of said signal occurs to generate a data element corresponding to one particular characteristic of the event, and electronically compensating said data elements for crosstalk between all other channels that cause errors in the data elements by receiving compensation signals in each channel from all the other channels and subtracting in each channel the sum of these compensation signals from said data element generated by said channel;

temporarily storing said data elements as they are gathered until all the data elements regarding a particular event are gathered; and reading the data regarding an event and comparing the data to the nodes of a binary classification tree and making a sort decision based upon the path taken through said binary classification tree based upon the results of each comparison.

12. The method of claim 11 further comprising the step of displaying on one or more two dimensional displays the data from which each sort decision is made.

13. An apparatus for making classification decisions in real time regarding a plurality of events comprising:

data gathering means including a plurality of light detectors for asynchronously gathering a plurality of digital data derived from signals generated by said light detectors from scattered and fluorescent light caused by objects tagged with fluorescing dyes which have been passed through a plurality of laser beams using a plurality of channel means for storing said data, said digital data defining a multi-dimensional space describing each said event and said data gathering means including means for temporarily storing said digital data in a separate FIFO buffer for each channel means, said data gathering means including an event detection means for detecting when an event occurs which will cause a pulse signal to occur in each said channel means, and for generating a sample signal upon occurrence of said event, and, after a delay tailored to match the individual delay for any particular channel before said pulse signal in that particular channel peaks, for sending said event signal to that particular channel, and for repeating this process for each said channel means, each said channel means including means to sample said pulse signal upon receipt of said event signal and for converting said sample to said digital data and storing said digital data in said separate FIFO buffer for that channel means, all said channel mean storing digital data pertaining to the same event in the same relative positions in said FIFO buffers, said data gathering means including attenuation means for attenuating the data gathered by each said channel means by a programmable amount and for outputting said attenuated data from each said channel means as a compensation signal, and further comprising compensation means in each said channel means for receiving said compensation signals from predetermined ones of said attenuation means in the other channel means and for summing the compensation signal received and further attenuating the data gathered by said channel means by an amount proportional to the sum of said compensation signals received from said predetermined ones of said attenuation means in said other channel means;

comparing means for resynchronizing the digital data pertaining to a particular event by retrieving the digital data pertaining to one event from selected ones of said FIFO buffers in said channel means and for comparing in real time said digital data regarding each said event to the nodes of a binary classification tree and including means for making a classification decision based upon the comparison results at each said node.

14. The apparatus of claim 13 further comprising a buffer means in said data gathering means for temporarily storing said digital data until it is needed by said comparing means.

15. The apparatus of claim 14 wherein said buffer means comprises a plurality of FIFO buffers.

16. The apparatus of claim 14 wherein said events being sorted correspond to said digital data derived by said data gathering means from scattered and fluorescence light from living or dead cells which are tagged with fluorescent dye, said cell being passed through at least one laser beam, and further comprising means for entraining said cells in a stream of conductive fluid, and further comprising means for passing said stream through the beam of at least one laser having a wavelength selected to excite said fluorescent dye, and further comprising at least two scattered light detectors and at least two fluorescent light detectors for detecting light emitted from said fluorescent dye and light scattered from said cells.

17. The apparatus of claim 16 wherein each cell has attached thereto at least two fluorescent dyes, and further comprising a second laser for emitting coherent light in a beam through which said cells pass, said light having a frequency to excite fluorescence in a different dye than was excited to fluorescence by the light from said first laser and wherein at least some of said light detectors are fluorescent light detectors for detecting fluorescent light emitted by said dyes.

18. The apparatus of claim 17 wherein said means for gathering includes a nozzle for guiding a stream of electrically conductive fluid containing said objects, and further comprising a drop charging electrode in electrical contact with said stream, and further comprising means for vibrating said nozzle so as to cause said stream to break up into droplets sized to carry at least one said object, and further comprising means for converting said classification decision into a drop charging signal and applying said drop charging signal to said drop charging electrode as the object to which said classification decision pertains reaches the point where said droplets are formed.

19. The apparatus of claim 18 wherein said attenuation means comprises means for reducing noise in the signals from said light detectors caused by sources other than the light to be detected by any particular detector.

20. The apparatus of claim 19 wherein said data gathering means includes a matched filter for each said light detector, said matched filter having filter characteristics matched to the characteristics of the signals generated by the corresponding said light detector in said data gathering means.

21. The apparatus of claim 20 wherein each said channel means further comprising an amplifier with a logarithmic transfer function and an amplifier with a linear transfer function, said apparatus for making classification decisions further comprising a user interface computer including means for allowing either said logarithmic or said linear amplifier to be selected to amplify the signals from the light detector corresponding to said channel means and further comprising means for selectably setting the gain of said linear amplifier through said user interface computer.

22. The apparatus of claim 21 further comprising means for sensing signals from said light detectors only if they are above a desired threshold, and for detecting the peaks of said signals and outputting an event signal at the time of occurrence of said peak.

23. The apparatus of claim 22 wherein each light detector corresponds to one said channel means, and further comprising a sample and hold amplifier in each said channel means for sampling the signal from the output of the selected amplifier and further comprising digital-to-analog conversion means for converting the sample value to a digital value and wherein the digital value from each digital-to-analog conversion means is stored in a separate FIFO buffer in each said channel means, and further comprising a separate delay means in each said channel means for each corresponding light detector, each said delay means having an input coupled to receive said event signal from said means for sensing and peak detecting and for delaying the output of said event signal by a programmable amount for each said light detector, and wherein said user interface computer includes means for selectably setting the desired amount of delay for each light detector, and wherein said event signal for each light detector is coupled to the corresponding sample and hold amplifier for that light detector to cause said sample and hold amplifier to sample the signal from said light detector.

24. The apparatus of claim 23 wherein said means for vibrating said nozzle is coupled to said user interface computer and wherein said user interface computer includes means for selectably setting the drop formation rate.

25. The apparatus of claim 24 further comprising two separate event FIFO buffers selectively coupled to the output of said FIFO buffers for storing the digital data from each light detector, one of said event FIFO buffers for storing the event data temporarily until said means for comparing can read the event data and make a classification decision, the other said event FIFO buffer for storing said event data until the classification decision is made and said user interface computer requests said event data and the corresponding classification decision, said user interface computer further comprising means for displaying said event data.

26. An apparatus for making classification decisions in real time comprising:
    means for collecting multidimensional analog data about an event;
    means for subtracting out noise from said data, and filtering said data to maximize the signal to noise ratio;
    means for converting said data to digital data by sampling said analog data at its peak and doing an analog to digital conversion on it;
    first means for temporarily storing said data while awaiting a classification decision;
    means for retrieving said selected data from said storage means and for comparing it to a classification decision tree and for generating a classification decision based upon said comparison;
    second means for temporarily storing said classification decisions until they are needed; and
    means for retrieving said classification decisions from said second means and for classifying said event based upon the classification decision retrieved from said second means pertaining to said event.

27. The apparatus of claim 26 wherein said data gathering means includes two lasers emitting coherent light at two different frequencies and a plurality of scattered light detectors and a plurality of fluorescent light detectors, each detector including means to block light from all but a single range of wavelengths tuned to the emission spectra of a particular dye in a plurality of dyes used to stain objects being illuminated by said lasers.

28. The apparatus of claim 27 further comprising means for compensating the signals from said light detectors such that the signal derived from each light detector after compensation has an amplitude which is due substantially solely to emissions from a single selected dye.

29. A method for classifying events in real time comprising the steps of:
    asynchronously, electronically gathering a plurality of data about an event, said data defining a multidimensional space having more than three dimensions;
    resynchronizing said asynchronously gathered data by storing said data in a plurality of first-in-first-out buffers, one such buffer being dedicated to each dimension of the multidimensional space such that all said data pertaining to a single event in said multidimensional space can be retrieved at substantially the same time when said event is to be classified;
    reading data about said event out of said first-in-first-out buffers and comparing said data in real time to data organized in the form of a binary classification tree;
    formulating in real time a classification decision based upon the results of the comparison against said binary classification tree;
    storing the classification decision in a buffer such that said classification decision can be retrieved later when said classification decision is needed to take action regarding the event to which it pertains; and
    retrieving in real time the classification decision regarding a particular event to be acted upon, and taking the action specified in the classification decision in real time.

30. The method of claim 29 wherein the step of gathering data includes the steps of shining light of a predetermined wavelength on objects having one or more fluorescent dyes on them capable of being excited by light of said predetermined wavelength and detecting the amount of scattered light at predetermined angles and the amount of light emitted by said dyes.

31. The method of claim 30 further comprising the step of filtering light emitted from said dyes such that a plurality of light detectors each receives light only in a specified band of wavelengths corresponding to the emission band of a particular one of said dyes.

32. The method of claim 31 further comprising the step of compensating the signals derived from said light detectors after filtering to eliminate the effects of light emitted in the passbands of the various filters generated by dyes the light from which is not desired in said passbands such that the signal derived from each light detector is caused substantially by only one dye.

33. The method of claim 32 wherein each said light detector emits a pulse when an object passes through said light, and further comprising the step of filtering the output of each said light detector so as to remove the average noise level, and of maximizing the signal to noise ratio by matched filtering of the pulse emitted from said light detector.

34. The method of claim 33 wherein the step of taking action on the classification decision includes the steps of interpreting the classification decision, converting each said classification decision to a pulse having a predetermined magnitude and polarity.

35. The method of claim 34 further comprising the steps of entraining objects to be sorted into a train of electrically conductive liquid flowing through a nozzle, vibrating the nozzle so as to break the stream into droplets some of which contain objects, shining coherent light on said stream of objects, using said pulses generated from each classification decision generated from data gathered about each object to charge the droplet containing said object as it breaks from said stream, and deflecting said charged droplet into a sorting bin designated for objects of that type.

* * * * *

UNITED STATES PATENT AND TRADEMARK OFFICE
CERTIFICATE OF CORRECTION

PATENT NO. : 4,987,539

DATED : January 22, 1991

INVENTOR(S) : Wayne A. Moore et al.

It is certified that error appears in the above-identified patent and that said Letters Patent is hereby corrected as shown below:

Column 23, line 2, "(3))" should read --(3)--.

Column 30, line 59, Claim 5, "samples" should read --sampled--.

Signed and Sealed this

Twenty-fourth Day of November, 1992

Attest:

DOUGLAS B. COMER

Attesting Officer      Acting Commissioner of Patents and Trademarks